(12) United States Patent
Hohlbaum et al.

(10) Patent No.: US 9,572,863 B2
(45) Date of Patent: Feb. 21, 2017

(54) METHODS FOR PREVENTING OR TREATING CERTAIN DISORDERS BY INHIBITING BINDING OF IL-4 AND/OR IL-13 TO THEIR RESPECTIVE RECEPTORS

(71) Applicant: PIERIS PHARMACEUTICALS GMBH, Freising-Weihenstephan (DE)

(72) Inventors: Andreas Hohlbaum, Paunzhausen (DE); Laurent Audoly, Mahwah, NJ (US); Beverly Koller, Chapel Hill, NC (US)

(73) Assignee: Pieris Pharmaceuticals GmbH, Freising-Weihenstephan (DE)

( * ) Notice: Subject to any disclaimer, the term of this patent is extended or adjusted under 35 U.S.C. 154(b) by 0 days.

(21) Appl. No.: 14/364,449

(22) PCT Filed: Dec. 12, 2012

(86) PCT No.: PCT/EP2012/075146
§ 371 (c)(1),
(2) Date: Jun. 11, 2014

(87) PCT Pub. No.: WO2013/087660
PCT Pub. Date: Jun. 20, 2013

(65) Prior Publication Data
US 2014/0357548 A1 Dec. 4, 2014

Related U.S. Application Data

(60) Provisional application No. 61/570,018, filed on Dec. 13, 2011.

(51) Int. Cl.
*A61K 38/00* (2006.01)
*A61K 38/17* (2006.01)
*A61K 9/00* (2006.01)
*A61K 9/08* (2006.01)

(52) U.S. Cl.
CPC ......... *A61K 38/1709* (2013.01); *A61K 9/0078* (2013.01); *A61K 9/08* (2013.01)

(58) Field of Classification Search
None
See application file for complete search history.

(56) References Cited

U.S. PATENT DOCUMENTS

2009/0305982 A1* 12/2009 Jensen ............... C07K 14/47
514/21.2

FOREIGN PATENT DOCUMENTS

| JP | 2009-545301 A | 12/2009 |
|---|---|---|
| WO | WO 2008/015239 A2 | 2/2008 |
| WO | WO 2008015239 A2 * | 2/2008 |
| WO | WO 2011/154420 A2 | 12/2011 |

OTHER PUBLICATIONS

Davidson et al., Genetics and pulmonary medicine. THORAX. 1998; 53:389-397.*
Holloway et al. Genetics of allergic disease. J Allergy Olin Immunol. vol. 125, No. 2, Feb. 2010, pp. S81-S94.*
Cowden et al., "Histamine H4 receptor antagonism diminishes existing airway inflammation and dysfunction via modulation of Th2 cytokines," Respiratory Research, 11:86, Jun. 2010 (12 pages).
European Office Action dated Jul. 10, 2015 issued in Application No. 12813295.8.
Fiset et al., "Modulation of allergic response in nasal mucosa by antisense oligodeoxynucleotides for IL-4," Journal of Allergy and Clinical Immunology, 111:580-586, Jan. 2003.
Moore et al, "IL-13 and IL-4 cause eotaxin release in human airway smooth muscle cells: a role for ERK," American Journal of Physiology. Lung Cellular and Molecular Physiology, 282:L847-L853, Nov. 2001.
Terada et al., "Contribution of IL-18 to atopic-dermatitis like skin inflammation induced by *Staphylococcus aureus* product in mice," PNAS, 103:8616-8821, Jun. 2006.
Walker et al., "RNA interference of State rapidly attenuates ongoing inter-leukin-13-mediated events in lung epithelial cells," Immunology, 127:256-266, Jun. 2009.
Loefblom et al., "Non-immunoglobulin based protein scaffolds," Current Opinion in Biotechnology, 2011, 22:843-848.
Hohibaurn et al., "Next generation therapeutics for the treatment of respiratory diseases—discovery and characterization of an inhalable highly potent and specific anti-IL-4RA small protein antagonist," Inflamm. Res., Jun. 2011, 60(Supp1):82-83, $10^{th}$ World Congress on Inflammation, Paris, France, Jun. 25-29, 2011.

(Continued)

*Primary Examiner* — Jeanette Lieb
(74) *Attorney, Agent, or Firm* — Foley & Lardner LLP

(57) ABSTRACT

The present disclosure relates to methods of treating, ameliorating or preventing a disorder comprising administering a therapeutically effective amount of a composition comprising a protein which inhibits IL-4 and/or IL-13 from binding to their respective receptors to a subject in need thereof. In some embodiments, the disorder is preferably associated with an increase of the Th2 immune response. In some embodiments, administration is preferably locally to the lung in order to treat, ameliorate or prevent allergic asthma, rhinitis, conjunctivitis, lung fibrosis, cystic fibrosis, chronic obstructive pulmonary disease, pulmonary alveolar proteinosis or adult respiratory distress syndrome.

20 Claims, 8 Drawing Sheets

(56) References Cited

OTHER PUBLICATIONS

Hirst, Stuart J., et al.; "Selective Induction of Eotaxin Release by Interleukin-3 or Interleukin-4 in Human Airway Smooth Muscle Cells is Synergistic with Interleukin-1β and is Mediated by the Interleukin-4 Receptor α—Chain"; American Journal of Respiratory and Critical Care Medicine, vol. 165, No. 8, pp. 1161-1171, 2002.

Japan Patent Office Notice of Reasons for Rejection issued in application 2014-546471 dated May 23, 2016; pp. 1-5 (with English translation).

\* cited by examiner

A

IL-13 induced Stat6 phosphorylation

B

IL-4 induced Stat6 phosphorylation

Inhibition of human IL-4 induced Stat6 prophorylation in splenocytes isolated from hIL-4RA/hIL-13RA1 knock-in mice Inhibition of Human IL-13 induced eotaxin expression in hIL-4RA/hIL-13RA1 knock-in mice

A

Inhibition of IL-13 induced Eotaxin RNA in the lung tissue of human IL-4RA/human IL-13 double knock-in mice (time course)

B

Inhibition of IL-13 induced Eotaxin RNA in the lung tissue of human IL-4RA/human IL-13 double knock-in mice (dose response)

Inhibition of IL-13 induced Eotaxin RNA in the lung tissue of human IL-4RA/human IL-13 double knock-in mice (comparison with IL-4 (R121D, Y124D))

HP-SEC analysis of starting material, nebulized and material remaining in reservoir T-remainder
T-nebulized
T0
Placebo

B

Laser diffraction of nebulized formulation

Time [sec]

Pharmacokinetic properties and biodistribution of a lipocalin mutein in human IL-4RA/human IL-13 double knock-in mice after intratracheal instillation

A

Calculated total amounts of the mutein in plasma, BALF and lung tissue

B

Measured plasma and lung tissue concentrations of the mutein in relation to an estimated $EC_{90}$ of 0,7µg/ml (dashed line)

Inhibition of IL-13 induced goblet cell metaplasia in
human airway epithelium air-liquid-interface culture system

A

Goblet cell surface area measured by Alcain blue staining (image analysis)

B

Phase contrast microscopy of Alcain blue stained epithelial/goblet cells

C

Alcain blue/Neutral red stained paraffin sections
without (negative) and with IL-13 (positive) on day 14

D

Eotaxin 3 in basal media of ALI culture on day 14

- lipocalin mutein (SEQ ID NO:6)
- lipocalin (SEQ ID NO:1)
- IL-4 (R121D, Y124D)
- anti-IL-4R mAb

METHODS FOR PREVENTING OR TREATING CERTAIN DISORDERS BY INHIBITING BINDING OF IL-4 AND/OR IL-13 TO THEIR RESPECTIVE RECEPTORS

CROSS-REFERENCE TO RELATED APPLICATIONS

This application is a National Stage application of PCT/EP2012/075146, filed Dec. 12, 2012, which claims priority from U.S. Provisional Application 61/570,018, filed Dec. 13, 2011.

The instant application contains a Sequence Listing which has been submitted in ASCII format via EFS-WEB and is hereby incorporated by reference in its entirety. Said ASCII copy, created on Aug. 12, 2014, is named sequence.txt and is 30 KB.

FIELD OF THE INVENTION

The present disclosure relates to methods of treating, ameliorating or preventing a disorder comprising administering a therapeutically effective amount of a composition comprising a protein which inhibits the ligand of Uniprot #P05112 and/or the ligand of Uniprot #P35225 from binding to their respective receptors to a subject in need thereof. In some embodiments, the disorder is preferably associated with an increase of the Th2 immune response. In some embodiments, administration is preferably locally to the lung in order to treat, ameliorate or prevent allergic asthma, rhinitis, conjunctivitis, lung fibrosis, cystic fibrosis, chronic obstructive pulmonary disease, pulmonary alveolar proteinosis or adult respiratory distress syndrome.

BACKGROUND

Proteins that selectively bind to selected targets by way of non-covalent interaction play a crucial role as reagents in biotechnology, medicine, bioanalytics as well as in the biological and life sciences in general. Antibodies, i.e. immunoglobulins, are a prominent example of this class of proteins. Despite the manifold needs for such proteins in conjunction with recognition, binding and/or separation of ligands/targets, almost exclusively immunoglobulins are currently used.

Additional proteinaceous binding molecules that have antibody-like functions are the members of the lipocalin family, which have naturally evolved to bind ligands. Lipocalins occur in many organisms, including vertebrates, insects, plants and bacteria. The members of the lipocalin protein family (Pervaiz, S., & Brew, K. (1987) FASEB J. 1, 209-214) are typically small, secreted proteins and have a single polypeptide chain. They are characterized by a range of different molecular-recognition properties: their ability to bind various, principally hydrophobic molecules (such as retinoids, fatty acids, cholesterols, prostaglandins, biliverdins, pheromones, tastants, and odorants), their binding to specific cell-surface receptors and their formation of macromolecular complexes. Although they have, in the past, been classified primarily as transport proteins, it is now clear that the lipocalins fulfill a variety of physiological functions. These include roles in retinol transport, olfaction, pheromone signaling, and the synthesis of prostaglandins. The lipocalins have also been implicated in the regulation of the immune response and the mediation of cell homoeostasis (reviewed, for example, in Flower, D. R. (1996) *Biochem. J.* 318, 1-14 and Flower, D. R. et al. (2000) *Biochim. Biophys. Acta* 1482, 9-24).

The lipocalins share unusually low levels of overall sequence conservation, often with sequence identities of less than 20%. In strong contrast, their overall folding pattern is highly conserved. The central part of the lipocalin structure consists of a single eight-stranded anti-parallel β-sheet closed back on itself to form a continuously hydrogen-bonded β-barrel. This β-barrel forms a central cavity. One end of the barrel is sterically blocked by the N-terminal peptide segment that runs across its bottom as well as three peptide loops connecting the β-strands. The other end of the β-barrel is open to the solvent and encompasses a target-binding site, which is formed by four flexible peptide loops. It is this diversity of the loops in the otherwise rigid lipocalin scaffold that gives rise to a variety of different binding modes each capable of accommodating targets of different size, shape, and chemical character (reviewed, e.g., in Flower, D. R. (1996), supra; Flower, D. R. et al. (2000), supra, or Skerra, A. (2000) *Biochim. Biophys. Acta* 1482, 337-350).

Various PCT publications (e.g., WO 99/16873, WO 00/75308, WO 03/029463, WO 03/029471 and WO 2005/19256) disclose how muteins of various lipocalins (e.g. tear lipocalin and hNGAL lipocalin) can be constructed to exhibit a high affinity and specificity against a target that is different than a natural ligand of a wild type lipocalin. This can be done, for example, by mutating one or more amino acid positions of at least one of the four peptide loops. In addition, PCT publication WO 2011/154420 teaches one or more methods for producing lipocalin muteins, which bind to IL-4 receptor subunit alpha.

Th2 cytokines IL-4 (officially known as Interleukin-4, Uniprot #P05112) and IL-13 (officially known as Interleukin-13, Uniprot #P35225) have largely overlapping functions and directly promote several key features of asthma including eosinophilia, goblet cell metaplasia, airway hyper-responisveness, IgE immunoglobin switch, alternative macrophage activation, smooth muscle cell remodeling and subepithelial fibrosis. Furthermore, genetic polymorphism in the genes of IL-4, IL-13, IL-4RA (officially known as Interleukin-4 receptor subunit alpha, Uniprot #P24394, SEQ ID NO: 12) and Stat6 are linked with Asthma. This is particular relevant as the combination of allelic variant of IL-4, IL-13, IL-4RA and Stat6 appear synergistic and described polymorphism in IL-4, IL-13 and IL-4RA enhance the production, function or signaling activity of the Th2 cytokines or common subunit of the IL-4/IL-13 receptor (Finkelman et al. JI, 2010, 184:1663-74). Recently, asthma endotypes or subphenotypes have been defined by molecular mechanism or treatment response. Woodruff et al for example defined asthma phenotypes into Th2-high and Th2-low based on the lung epithelial expression of IL-13-inducible genes POSTN (periostin), CLCA1 (gobs) and SERPINB2 (Wooddruff P G et al, Genome-wide profiling identifies epithelial cell genes associated with asthma and with treatment response to corticosteroids PNAS, 2007, 104: 15858-63; Prescott G. Woodruff) (T-helper Type 2-driven inflammation defines major subphenotypes of Asthma, Am. J. Respir. Crti. Care Med., 2009, 180:388-395).

Therefore, it would be desirable to have improved therapeutic methods involving therapeutically effective amount of a composition comprising muteins of human tear lipocalin, binding to IL-4RA with high binding affinity and therefore inhibiting IL-4 and/or IL-13 from binding to their respective receptors, that exhibit in vivo therapeutic activities in a subject in need thereof. When used in the present application, a subject in need thereof may be a mammal, such as a human, a dog, a mouse, a rat, a pig, an ape such as cynomolgus to name only a few illustrative examples, which is in need of a treatment or prevention of a disorder.

SUMMARY OF THE DISCLOSURE

The present disclosure relates to a method of treating, ameliorating or preventing a disorder comprising administering a therapeutically effective amount of a composition to a subject in need of such composition, wherein said composition comprises a lipocalin mutein of the disclosure that is capable of inhibiting IL-4 and/or IL-13 from binding to their respective receptors. In some further embodiment, the lipocalin mutein is capable of disrupting downstream signaling and/or cellular responses induced by IL-4 and/or IL-13. In various embodiments, the disorder is a disorder in which the IL4/IL13 pathway contributes to disease pathogenesis. In various further embodiments, the composition may be locally administered to the lung. In various preferred embodiments, the composition may be administered via aerosol inhalation. In some still preferred embodiments, the composition is administered to a subject in need thereof at a frequency selected from the group consisting of: up to four times daily, up to three times daily, up to twice daily, up to once daily, up to once every other day, up to once every third day, up to once every week and up to once every other week.

In some embodiments, when used in the present application, a subject in need of such composition is suffering from a disorder in which the IL-4 expression and/or IL-13 expression contributes or is related to disease pathogenesis or aggravation. In some embodiments, the subject, in need of such composition, is suffering from a disorder that can be improved, ameliorated or inhibited by removal, inhibition or reduction of the IL-4 activity and/or IL-13 activity. In some further embodiments, a subject in need of such composition may be suffering from one or more disorders including, for example, allergic inflammation, allergic asthma, rhinitis, conjunctivitis, lung fibrosis, cystic fibrosis, chronic obstructive pulmonary disease, pulmonary alveolar proteinosis or adult respiratory distress syndrome. It is also envisaged that the lipocalin mutein of the disclosure, in some embodiments, is applied for the treatment, amelioration or prevention of tissue fibrosis (see Chiaramonte et al. (1999), J. Clin. Invest. 104(6), 777-785. The fibrosis may preferably result from healing of a wound, for example, a wound from a surgical incision. The tissue fibrosis affects, for example, a tissue selected from the group consisting of liver, skin epidermis, skin endodermis, muscle, tendon, cartilage, cardiac tissue, pancreatic tissue, lung tissue, uterine tissue, neural tissue, testis, ovary, adrenal gland, artery, vein, colon, small intestine, biliary tract and gut, in particular, the tissue being selected from lung and liver.

For example, one disorder that can be preferably treated, ameliorated or prevented by a method of the disclosure is associated with an increase of the Th2 immune response.

In some embodiments, the disorder can be associated with an allergic reaction or an allergic inflammation, preferably, the allergic reaction is a food allergy, and preferably, the allergic inflammation is associated with allergic asthma, rhinitis, conjunctivitis or dermatitis. In various preferred embodiments, the allergic asthma can be an airway inflammation in which the IL4/IL13 pathway contributes to disease pathogenesis.

In other preferred embodiments, the composition of the disclosure further comprises an anti-allergic medicament and/or an anti-allergic inflammation medicament.

Another exemplary disorder that can be preferably treated, ameliorated or prevented by a method of the disclosure is associated with a mucus production or a mucus secretion.

In various preferred embodiments, the disorder can be a lung disorder, and preferably a chronic obstructive pulmonary disease (COPD) or cystic fibrosis (CF).

In a still further embodiment, the said composition can be used as a gene therapy agent for various disclosed disorders.

A lipocalin mutein of the disclosure can be a human tear lipocalin mutein which has at any one or more amino acids at a position corresponding to position 27, 28, 30, 31, 33, 53, 57, 61, 64, 66, 80, 83, 104-106 and 108 of the linear polypeptide sequence of the mature human tear lipocalin a mutated amino acid. However, the lipocalin mutein of the disclosure can also be a mutein of a lipocalin other than human tear lipocalin, such as human NGAL lipocalin or other lipocalins described herein.

In various preferred embodiments, the lipocalin mutein has at any two or more amino acids at a position corresponding to position 26, 32, 34, 55, 56, 58 and 63 of the linear polypeptide sequence of the mature human tear lipocalin a mutated amino acid.

The lipocalin mutein described herein has in a particularly preferred embodiment at least 75% identity to the sequence of mature human tear lipocalin (SEQ ID NO: 1).

A lipocalin mutein applied in the methods of the present disclosure is preferably cross-reactive with another species, e.g. marmoset IL-4RA, which allows testing of the then-candidate lipocalin mutein in marmoset apes resembling the human organism. The lipocalin mutein may or may not be cross-reactive with IL-4RA from other non-human species such as mouse IL-4RA and/or cynomolgus IL-4RA.

It is generally preferred that the lipocalin mutein is essentially not cross-reactive with a related protein or non-related protein. Said related protein is, for example, an IL-23 receptor alpha chain and/or type I cytokine receptor with fibronectin type III domain, while said non-related protein is, for example, an IL-6 receptor and/or IL-18 receptor alpha chain.

DESCRIPTION OF THE FIGURES

FIG. 5 depicts the analysis of a nebulized lipocalin mutein by size exclusion chromatography and laser diffraction.

DETAILED DESCRIPTION

Figure 1:
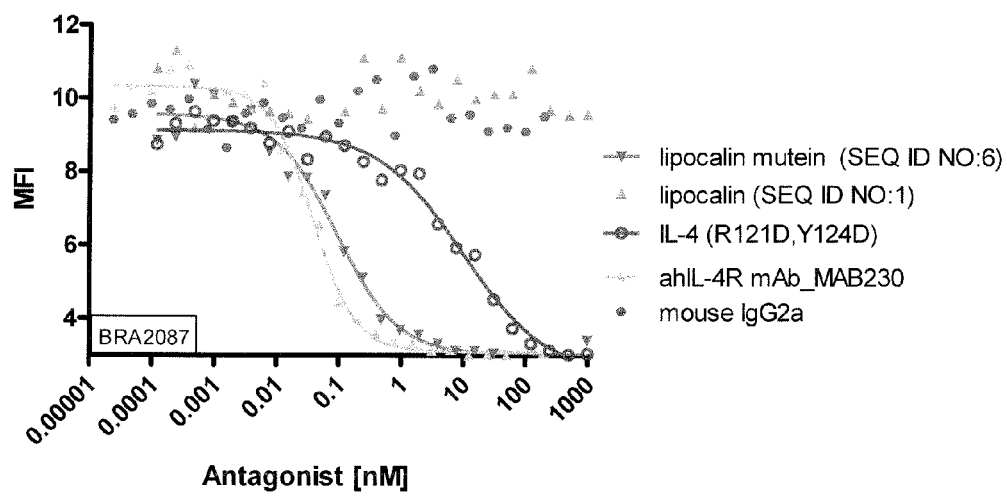
FIG. 1 depicts inhibition of human IL-4 and IL-13 induced STAT 6 phosphorylation (FACS-based assay) in TF-1 cells by a lipocalin mutein of the disclosure.
Figure 1:
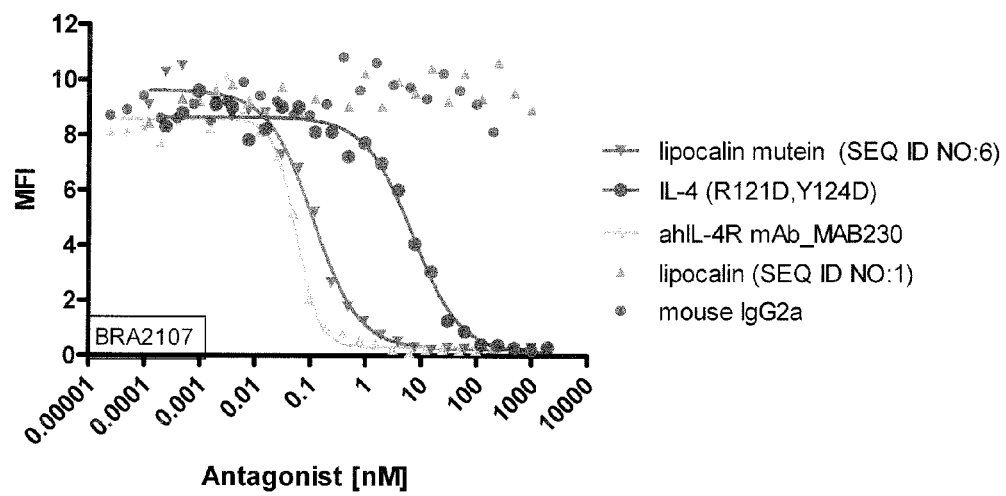

The present disclosure provides a method of treating, ameliorating or preventing a disclosed disorder, comprising administering a therapeutically effective amount of a composition comprising a lipocalin mutein, which inhibits IL-4 and/or IL-13 from binding to their respective receptors by binding to IL-4 receptor alpha chain, to a subject in need thereof. A lipocalin mutein for use in accordance with the present disclosure can specifically bind to IL-4 receptor alpha chain. Advantageously, these lipocalin muteins have a high binding affinity for the IL-4 receptor alpha chain. These lipocalin muteins have even improved binding properties for IL-4 receptor alpha in relation to the lipocalin muteins provided in WO 2008/015239; in particular, they have a higher binding affinity.

The present inventors have demonstrated that lipocalin muteins of the present disclosure, due to their binding of the IL-4 receptor alpha chain, interfere with the interaction of the receptors' cognate ligands, i.e., the cytokine(s) IL-4 and/or IL-13, in a manner to bring about a therapeutic response in vivo. For example, data from a transgenic mouse model, which was used to investigate effects that lipocalin muteins of the disclosure may have on IL-4 and/or IL-13 mediated signaling, demonstrate a disruption of downstream signaling mediated by IL-4 and IL-13. The transgenic mouse, which resembles a human in that the mice carry genes encoding the human IL-4 receptor alpha chain and the IL-13 receptor alpha 1 chain, are representative of the therapeutic potential in humans. To this end, the human genes are located in their corresponding locus of the respective mouse chromosome, thereby rendering the mouse to be a double knock-in mouse expressing both the type I and type II receptor. Therefore, when used herein a "therapeutically effective amount" is preferably an amount of a lipocalin mutein of the present disclosure that is therapeutically effective in a human.

In contrast with Examples of the disclosure, the prior art does not teach the skilled person whether a lipocalin mutein of the disclosure is capable of is capable of disrupting downstream signaling or cellular responses induced by IL-4 and/or IL-13 in subjects, and/or capable of exhibiting an in vivo therapeutic activity in subjects suffering from one or more disorders, such as, allergic inflammation, allergic asthma, rhinitis, conjunctivitis, lung fibrosis, cystic fibrosis, chronic obstructive pulmonary disease, pulmonary alveolar proteinosis or adult respiratory distress syndrome. Nor can any information about the effectiveness of lipocalin muteins against these disorders be derived from the prior art. In the absence of any data demonstrating a therapeutic effect of a lipocalin mutein against disorders, for instance, associated with an increase of the Th2 immune response and/or with an allergic reaction or an allergic inflammation, such therapeutic effect and corresponding methods of treatment, prevention or amelioration could not reasonably have been expected.

Indeed, the present disclosure provides in vivo data showing a therapeutic effect of the lipocalin muteins described herein which illustrate, for example, the anti-inflammatory effect of the lipocalin muteins of the present disclosure. In this regard, the present disclosure shows, for the first time, that a lipocalin mutein of the disclosure (SEQ ID NO: 6) is capable of inhibiting human IL-13 induced transcript Ccl11 (eotaxin) effectively in vivo and is more potent than an IL-4 mutant (the IL-4 (R121D, Y124D) in FIG. 4c) as measured by a test essentially described in Example 5:

prepare several human IL-4 receptor alpha/human IL-13 receptor alpha chain 1 double knock-in mice as described in Example 4 with the exception that 30 µl of IL-13 (Peprotech, 1 µg) was administered by intratracheal instillation only once, optionally, set the test parameters as described in Example 5 and group the mice accordingly, apply the lipocalin mutein (SEQ ID NO: 6) by intratracheal instillation with a volume of 30 µl either at a constant dose of 98 µg at different times prior to the IL-13 dose or at different amounts 30 minutes prior to the IL-13 dose, apply the IL-4 mutant (R121D, Y124D) also by intratracheal instillation with a volume of 30 µl at different amounts 30 minutes prior to the IL-13 dose, use the abbreviated IL-13 induced airway inflammation model (single IL-13 intratracheal administration) to assess the duration of the pharmacological response, dose dependency and comparable potency.

The therapeutic effect observed on the murine animal model applied in the present disclosure thus provides sufficient evidence of a therapeutic application, given the presence of human orthologues and absence of murine orthologues. Based upon the this principle, it is more than reasonable that, in the absence of any data on human patients, the in vivo experiment are sufficiently predictive of the in vivo activity, for example the in vivo anti-inflammatory activity, of the lipocalin muteins described herein in humans.

Figure 7:
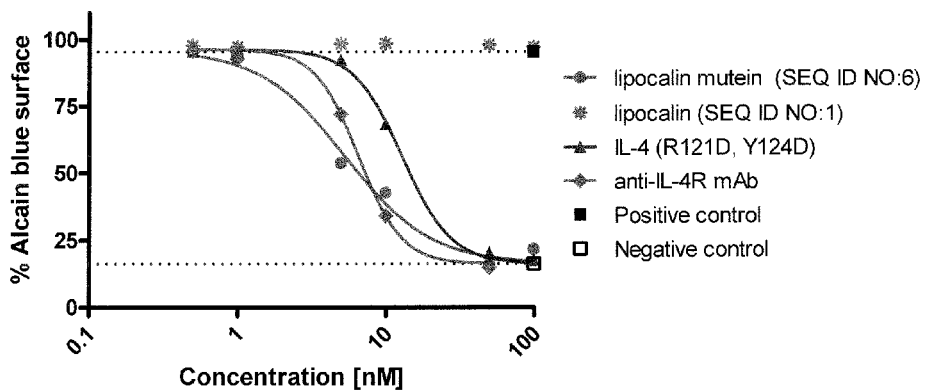
FIG. 7 depicts the inhibition of IL-13 induced goblet cell metaplasia in human airway epithelium air-liquid-interface culture system by a lipocalin mutein of the disclosure.
Figure 7:
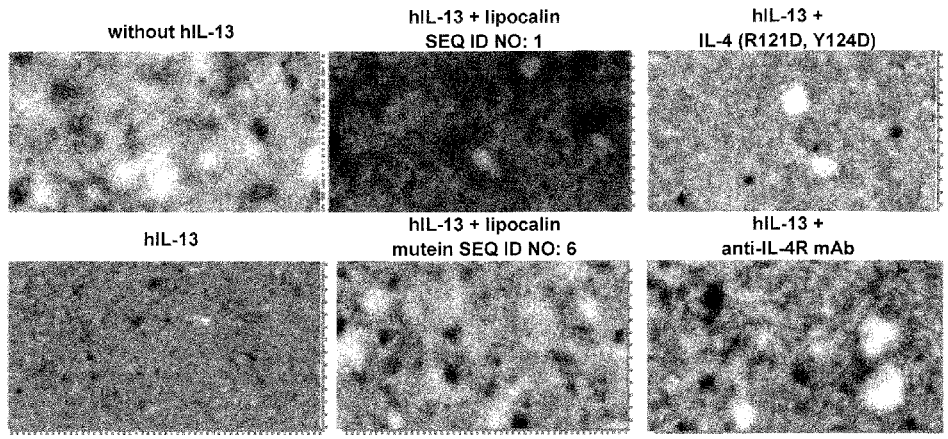
Figure 7:
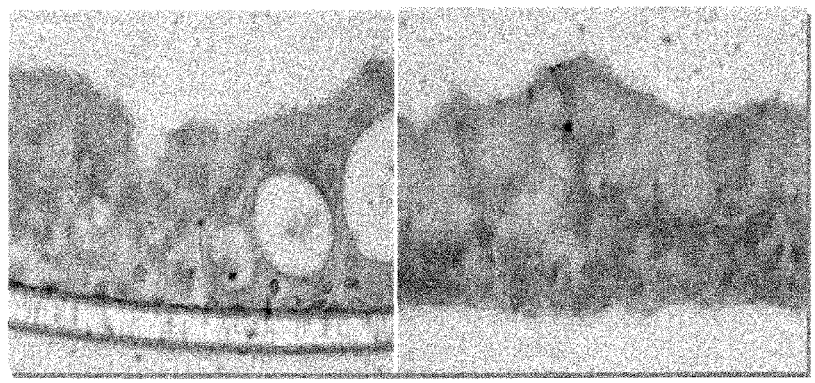
Figure 7:
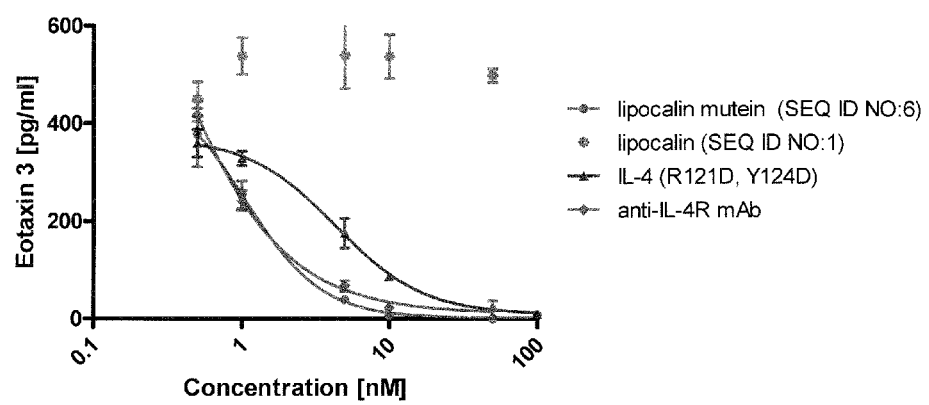

In addition, the present disclosure demonstrates that a lipocalin mutein of the disclosure (SEQ ID NO: 6) is capable of exhibiting a functional activity as good as an anti-IL-4RA monoclonal antibody (the anti-IL4R mAb in FIG. 7; the light and heavy chain variable region of which are shown in SEQ ID NOs: 14 and 15, respectively) disclosed in Example 8, as measured by a test essentially described in Example 8:

treat MucilAir™ (an air-liquid interface culture system with human airway epithelium reconstituted in vitro using primary human cells) every two days with human IL-13 at about 0.3 to 30 ng/ml, optionally, perform an in-situ Alcain blue stain (stains acid mucopolysacharides and glycosaminoglycans in blue to bluish-green), and/or perform histological analysis, in order to demonstrate that MucilAir™ shows an increased goblet cell density after about 14 days of treatment, test the inhibitory effect of a lipocalin mutein on goblet cell metaplasia by comparing continuous exposure of MucilAir™ to about 10 ng/ml human IL-13 for 14 days as positive control, to IL-13 plus different concentrations of a lipocalin mutein, to IL-13 plus different concentrations of said anti-IL-4RA monoclonal antibody (the light and heavy chain variable region are shown in SEQ D NOs: 14 and 15), and to MucilAir™ cultured for 14 days without IL-13 as negative control, perform an Alcain blue stain, e.g., dd Alcain blue stain to the apical surface for an in-situ stain and take pictures from stained cells under a phase contrast microscope for image analysis, quantify the percentage of the Alcain blue positive cells by the public domain Java image processing program ImageJ and express their number as area ratio of Alcain blue area/total image area, optionally, measure eotaxin-3 (an IL-13 induced chemokine) in the basal medium on day 14 using a commercially available ultrasensitive eotaxin-3 Kit from, e.g. Meso Scale Discovery.

Said anti-IL-4RA antibody has the variable light and heavy chain regions of SEQ ID NOs: 14 and 15, respectively, and was developed by Amgen (former Immunex) and is called AMG 317. It is a fully human monoclonal antibody that was under investigation for its ability to block the actions of interleukin-4 and interleukin-13 that play a role in asthma (in 2008, a phase 2 dose ranging study in moderate to severe asthma was completed). An interim analysis showed evidence of biological activity; however, the overall clinical efficacy did not meet the expectations. Thus, the lipocalin mutein of SEQ ID NO: 6 is capable of inhibiting IL-13 induced goblet cell metaplasia as good as the anti-IL-4RA monoclonal antibody described herein, when the comparison of the lipocalin mutein with said anti-IL-4RA antibody was done as described above. It is preferred in some further embodiments, therefore, that a lipocalin mutein of the disclosure has in the above-described test the same properties as the lipocalin mutein of SEQ ID NO: 6 with respect to the inhibition of goblet cell metaplasia.

The IL-4/IL-4Rα complex can dimerize with either the common gamma chain (γc, CD132) or the IL-13Ralpha1 (IL-13Rα1) subunit, via domains on IL-4, to create two different signaling complexes, commonly referred to as Type I and Type II receptors, respectively. Alternatively, IL-13 can bind IL-13Rα1 to form an IL-13/IL-13Rα1 complex that recruits the IL-4Rα subunit to form a Type II receptor complex. Thus, IL-4Rα mediates the biological activities of both IL-4 and IL-13 (reviewed by Gessner et al, Immunobiology, 201:285, 2000). The lipocalin muteins of the present disclosure advantageously interfere with and/or block the signaling via the Type I and/or Type II receptors, since these lipocalin muteins are capable of binding to the IL-4 receptor alpha chain.

In vitro studies have shown that IL-4 and IL-13 activate effector functions in a number of cell types, for example in T cells, B cells, eosinophils, mast cells, basophils, airway smooth muscle cells, respiratory epithelial cells, lung fibroblasts, and endothelial cells (reviewed by Steinke et al, Resp Res, 2:66, 2001, and by Willis-Karp, Immunol Rev, 202: 175, 2004). IL-4Rα is expressed in low numbers (100-5000 molecules/cell) on a variety of cell types (Lowenthal et al, J Immunol, 140:456, 1988), e.g. peripheral blood T cells, monocytes, airway epithelial cells, B cells and lung fibroblasts. The type I receptor predominates in hematopoietic cells, whereas the type II receptor is expressed on both hematopoietic cells and non-hematopoietic cells.

The cell surface receptors and receptor complexes bind IL-4 and/or IL-13 with different affinities. The principal components of receptors and receptor complexes that bind IL-4 and/or IL-13 are IL-4Rα, IL-13Rα1 and IL-13Rα2. These chains are expressed on the surface of cells as monomers or heterodimers of IL-4Rα/IL-13Rα1 or IL-4Rα/IL-13Rα2. IL-4-rα monomer binds IL-4, but not IL-13. IL-13Rα1 and IL-13Rα2 monomers bind IL-13, but do not bind IL-4. IL-4Rα/IL-13Rα1 and IL-4Rα/IL-13Rα2 heterodimers bind both IL-4 and IL-13. Given the fact that the IL-13 receptor alpha 2 (IL-13Ralpha2) that binds IL-13 with high affinity, but is a non-signaling receptor which is believed to be a decoy receptor for IL-13, it is envisaged that the lipocalin muteins of the present disclosure do preferably not bind to the IL-13 receptor alpha 2.

As explained, both IL-4 and IL-13 signal via the IL-4Rα, a component of the type I (IL-4Rα and γc) and type II receptors (IL-4Rα and IL-13Rα1). IL-4 signals via both type I and II receptor pathways, whereas IL-13 signals only via the type II IL-4R. IL-13 also binds to the IL-13Rα2 chain, which does not contain a trans-membrane-signaling domain and is thought to act as a decoy receptor. γc activates Janus kinase (JAK)3, whereas IL-13Rα1 activates tyrosine kinase 2 (TYK2) and JAK2. Activated JAKs then phosphorylate STAT-6. Phosphorylated STAT-6 dimerizes, migrates to the nucleus, and binds to the promoters of the IL-4 and IL-13 responsive genes, such as those associated with T-helper type 2 (Th2) cell differentiation, airway inflammation, airway hyper-responsiveness (AHR) and mucus production.

Th2-type immune responses promote antibody production and humoral immunity, and are elaborated to fight off extracellular pathogens. Th2 cells are mediators of Ig production (humoral immunity) and produce IL-4, IL-5, IL-6, IL-9, IL-10 and IL-13 (Tanaka, et. al., Cytokine Regulation of Humoral Immunity, 251-272, Snapper, ed., John Wiley and Sons, New York (1996)). Th2-type immune responses are characterized by the generation of certain cytokines (e.g., IL-4, IL-13) and specific types of antibodies (IgE, IgG4) and are typical of allergic reactions, which may result in watery eyes and asthmatic symptoms, such as airway inflammation and contraction of airway muscle cells in the lungs.

In addition, the disorder that is preferably treated, ameliorated or prevented by the methods of the present disclosure by applying the lipocalins as described herein, may be associated with allergic reaction or allergic inflammation.

In some preferred embodiments, the disorder may be allergic asthma, rhinitis, conjunctivitis or dermatitis.

Asthma is a complex, persistent, inflammatory disease characterized by airway hyper-responsiveness in association with airway inflammation. Studies suggest that regular use of high-dose inhaled corticosteroids and long-acting bronchodilators or omalizumab (a humanized monoclonal antibody that binds to immunoglobulin E and is often used as next-step therapy) may not be sufficient to provide asthma control in all patients, highlighting an important unmet need. Interleukin-4, interleukin-13, and the signal transducer and activator of transcription factor-6 are key components in the development of airway inflammation, mucus production, and airway hyper-responsiveness in asthma. Biological compounds targeting these molecules may provide a new therapeutic modality for patients with uncontrolled moderate to severe asthma. The present disclosure provides these biological compounds by way of the lipocalin muteins as described herein.

In some preferred embodiments, the allergic asthma is an airway inflammation in which the IL4/IL13 pathway contributes to disease pathogenesis.

Furthermore, the disorder that is preferably treated, ameliorated or prevented by the methods of the present disclosure by applying the lipocalins as described herein, may also be lung disorders, for example, pulmonary disorders in which the IL4/IL13 pathway contributes to disease pathogenesis. Such pulmonary disorders include but are not limited to, lung fibrosis, including chronic fibrotic lung disease, other conditions characterized by IL-4-induced fibroblast proliferation or collagen accumulation in the lungs, pulmonary conditions in which a Th2 immune response plays a role, conditions characterized by decreased barrier function in the lung (e.g., resulting from IL-4- induced damage to the epithelium), or conditions in which IL-4 plays a role in an inflammatory response.

Similarly, Cystic fibrosis (CF) is characterized by the overproduction of mucus and development of chronic infections. Inhibiting IL-4RA and the Th2 response will reduce mucus production and help control infections such as allergic bronchopulmonary aspergillosis (ABPA). Allergic bronchopulmonary mycosis occurs primarily in patients with cystic fibrosis or asthma, where a Th2 immune response is dominant. Inhibiting IL-4RA and the Th2 response will help clear and control these infections.

Similarly, chronic obstructive pulmonary disease (COPD) is associated with mucus hypersecretion and fibrosis. Inhibiting IL-4RA and the Th2 response will reduce the production of mucus and the development of fibrous thereby improving respiratory function and delaying disease progression. Bleomycin-induced pneumopathy and fibrosis, and radiation-induced pulmonary fibrosis are disorders characterized by fibrosis of the lung which is manifested by the influx of Th2, $CD4^{+}$ cells and macrophages, which produce IL-4 and IL-13 which in turn mediates the development of fibrosis. Inhibiting IL-4RA and the Th2 response will reduce or prevent the development of these disorders.

Moreover, IL-4 and IL-13 induce the differentiation of lung epithelial cells into mucus-producing goblet cells. IL-4 and IL-13 may therefore contribute to an enhanced production of mucus in subpopulations or some situations. Mucus production and secretion contributes to disease pathogenesis in chronic obstructive pulmonary disease (COPD) and cystic fibrosis (CF). Thus, the disorder, associated with a mucus production or a mucus secretion (for example, overproduction or hypersecretion), can be preferably treated, ameliorated or prevented by the methods of the present disclosure by applying a lipocalin mutein as described herein. In some preferred embodiments, the disorder, associated with a mucus production or a mucus secretion is preferably a chronic obstructive pulmonary disease (COPD) or a cystic fibrosis (CF). In other preferred embodiments, the composition of the disclosure further comprises an anti-mucus medicament.

Pulmonary alveolar proteinosis is characterized by the disruption of surfactant clearance. IL-4 increases surfactant product. In some further embodiments, use of an IL-4RA antagonist such as a lipocalin mutein of the disclosure to decrease surfactant production and decrease the need for whole lung lavage, is also contemplated herein.

Adult respiratory distress syndrome (ARDS) may be attributable to a number of factors, one of which is exposure to toxic chemicals. Therefore, as a preferred but non-limiting example, one patient population susceptible to ARDS is critically ill patients who go on ventilators, as ARDS is a frequent complication in such patients. In some further embodiments, an IL-4RA antagonist such as a lipocalin mutein of the disclosure may thus be used to alleviate, prevent or treat ARDS by reducing inflammation and adhesion molecules.

Sarcoidosis is characterized by granulomatous lesions. In some further embodiments, use of an IL-4RA antagonist such as a lipocalin mutein of the disclosure to treat sarcoidosis, particularly pulmonary sarcoidosis, is also contemplated herein.

Conditions in which IL-4-induced barrier disruption plays a role (e.g., conditions characterized by decreased epithelial barrier function in the lung) may be treated with IL-4RA antagonist(s). Damage to the epithelial barrier in the lungs may be induced by IL-4 and/or IL-13 directly or indirectly. The epithelium in the lung functions as a selective barrier that prevents contents of the lung lumen from entering the submucosa. A damaged or "leaky" barrier allows antigens to cross the barrier, which in turn elicits an immune response that may cause further damage to lung tissue. Such an immune response may include recruitment of eosinophils or mast cells, for example. An IL-4RA antagonist may be administered to inhibit such undesirable stimulation of an immune response.

In this regards, an IL-4RA antagonist such as a lipocalin mutein of the disclosure may be employed to promote healing of lung epithelium, in asthmatics for example, thus restoring barrier function, or alternatively, administered for prophylactic purposes, to prevent IL-4 and/or IL-13-induced damage to lung epithelium.

It should be noted that methods for treating a disease or disorder in accordance with the present disclosure are not limited by a particular mechanism of action. For example, in some further embodiments, the lipocalin mutein of the disclosure may be utilized as gene therapy agents in disclosed methods.

As used herein, "treatment" refers to clinical intervention in an attempt to alter the natural course of the subject or cell being treated, and can be performed before or during the course of clinical pathology. Desirable effects of treatment include preventing the occurrence or recurrence of a disease or a condition or symptom thereof, alleviating a condition or symptom of the disease, diminishing any direct or indirect pathological consequences of the disease, decreasing the rate of disease progression, ameliorating or palliating the disease state, and achieving remission or improved prognosis. In some embodiments, methods and compositions of the disclosure are useful in attempts to delay development of a disease or disorder. The treatment is applicable to both human therapy and veterinary applications.

"Prevention" includes that the disorders (or symptoms associated therewith) described herein may be avoided before they occur and/or that the disorders do not recur.

"Amelioration" includes that the disorders (or symptoms associated therewith) described herein are alleviated, diminished, decreased and/or palliated.

The term "administered" or "administering" in all of its grammatical forms means administration of a therapeutically effective dose of the lipocalin mutein as the sole therapeutic agent or in combination with another therapeutic agent as described herein to a subject. It is thus envisaged that a lipocalin mutein of the present disclosure is preferably in the form of a composition, preferably pharmaceutical composition, that may preferably be employed in co-therapy approaches, i.e. in co-administration with other medicaments or drugs, for example, other medicaments for treating a disorder as described herein and/or any other therapeutic agent which might be beneficial in the context of the methods of the present disclosure. Thus, it is preferred that a composition comprising the lipocalin muteins described herein further comprises an anti-allergic medicament and/or anti-allergic inflammation medicament.

An "effective amount", as used herein, refers to an amount effective, at dosages and for periods of time necessary of a lipocalin mutein as described herein, to achieve the desired therapeutic or prophylactic result. The exact dose will depend on the purpose of the treatment, and will be ascertainable by one skilled in the art using known techniques.

By "therapeutically effective amount" it is meant a dose that produces the effects for which it is administered. A "therapeutically effective amount" of a lipocalin mutein as described herein may vary according to factors such as age, body weight, general health, sex, diet, time of administration, drug interaction and the severity of the condition may be necessary, and will be ascertainable with routine experimentation by those skilled in the art. Sometimes, the term "therapeutically effective amount" may sometimes be interchangeably used herein with the term "pharmaceutically effective amount":

A therapeutically effective amount, when used in the present application, is also one in which any toxic or detrimental effects of the lipocalin mutein are outweighed by the therapeutically beneficial effects. A "prophylactically effective amount" refers to an amount effective, at dosages and for periods of time necessary of a lipocalin mutein as described herein, to achieve the desired prophylactic result. Typically but not necessarily, since a prophylactic dose is used in subjects prior to or at an earlier stage of disease, the prophylactically effective amount will be less than the therapeutically effective amount. The lipocalin mutein described herein having the desired therapeutic activity may be administered in a physiologically acceptable carrier to a patient, as described herein.

In some embodiments, a "subject", when used in the present application, is a vertebrate. In certain particular embodiments, the vertebrate is a mammal. Mammals include, but are not limited to, primates (including human and non-human primates) and rodents (e.g., mice and rats). In certain particular embodiments, a mammal subject is a human. In some further embodiments, a human subject, synonymous with an individual, is a particularly preferred subject. In some still further embodiments, a human subject in need thereof, when used in the present application, is a patient.

A protein of the disclosure can be a mutein of a lipocalin, preferably a lipocalin selected from the group consisting of retinol-binding protein (RBP), bilin-binding protein (BBP), apolipoprotein D (APO D), neutrophil gelatinase associated lipocalin (NGAL), tear lipocalin (TLPC), $\alpha_2$-microglobulin-related protein (A2m), 24p3/uterocalin (24p3), von Ebners gland protein 1 (VEGP 1), von Ebners gland protein 2 (VEGP 2), and Major allergen Can f1 precursor (ALL-1), with human NGAL being a preferred lipocalin and human tear lipocalin being a more preferred lipocalin. As used herein, a "lipocalin" is defined as monomeric protein of approximately 18-20 kDA in weight, having a cylindrical β-pleated sheet supersecondary structural region comprising a plurality of (preferably eight) β-strands connected pairwise by a plurality of (preferably four) loops at one end to define thereby a binding pocket. It is the diversity of the loops in the otherwise rigid lipocalin scaffold that gives rise to a variety of different binding modes among the lipocalin family members, each capable of accommodating targets of different size, shape, and chemical character (reviewed, e.g., in Skerra, A. (2000) Biochim. Biophys. Acta 1482, 337-350). Indeed, the lipocalin family of proteins have naturally evolved to bind a wide spectrum of ligands, sharing unusually low levels of overall sequence conservation (often with sequence identities of less than 20%) yet retaining a highly conserved overall folding pattern. The correspondence between positions in various lipocalins is well known to one of skill in the art. See, for example, U.S. Pat. No. 7,250,297.

Generally when referred to herein the disclosure, a lipocalin mutein of the disclosure, preferably, is different from its naturally occurring counterpart lipocalin in that it differs in at least one amino acid from its naturally occurring counterpart lipocalin. The difference might be an amino acid substitution, deletion and/or addition, with a substitution being preferred. In certain particular embodiments, a "mutein of a lipocalin" or "lipocalin mutein" can, in particular, be a "mutein of human tear lipocalin" or "Tlc mutein".

In a preferred embodiment, a protein of the disclosure is a mutein of human tear lipocalin (Tlc). The term "human tear lipocalin" as used herein to refer to the mature human tear lipocalin with the SWISS-PROT Data Bank Accession Number P31025. Mature human tear lipocalin (amino acids 19-176 of SWISS-PROT Accession Number P31025 acid sequence) (SEQ ID NO: 1) does not include the N-terminal signal peptide (amino acids 1-18) that is included in the sequence of SWISS-PROT Accession Number P31025 acid sequence used as the "reference" or "reference sequence" in various embodiments described herein.

Human tear pre-albumin, now called tear lipocalin (TLPC or Tlc), was originally described as a major protein of human tear fluid (approximately one third of the total protein content) but has recently also been identified in several other secretory tissues including prostate, nasal mucosa and tracheal mucosa. Homologous proteins have been found in rat, pig, dog and horse. Tear lipocalin is an unusual lipocalin member because of its high promiscuity for relative insoluble lipids and binding characteristics that differ from other members of this protein family (reviewed in Redl, B. (2000) Biochim. Biophys. Acta 1482, 241-248). A remarkable number of lipophilic compounds of different chemical classes such as fatty acids, fatty alcohols, phospholipids, glycolipids and cholesterol are endogenous ligands of this protein. Interestingly, in contrast to other lipocalins the strength of ligand (target) binding correlates with the length of the hydrocarbon tail both for alkyl amides and fatty acids. Thus, tear lipocalin binds most strongly the least soluble lipids (Glasgow, B J. et al. (1995) Curr. Eye Res. 14, 363-372; Gasymov, O. K. et al. (1999) Biochim. Biophys. Acta 1433, 307-320).

Lipocalin muteins particularly suitable for a therapeutic use as disclosed herein include the lipocalins set forth in SEQ ID NOs: 2-11. These molecules exhibit a specificity and high affinity for human IL4Ra, but prior the present disclosure have not been characterized with therapeutically relevant in vivo data. Other lipocalin muteins that are also suitable for a therapeutic use as disclosed herein include the lipocalins set forth in SEQ ID NOs: 2-8 of WO 2008/015239, each of these sequences is incorporated herein by reference. Further lipocalin muteins that may also be suitable for a therapeutic use as disclosed herein include the lipocalins set forth in SEQ ID NOs: 2-11 of WO 2011/154420, each of these sequences is incorporated herein by reference.

As used herein, a "mutein," a "mutated" entity (whether protein or nucleic acid) or "mutant" refers to the exchange (substitution), deletion, or insertion of one or more nucleotides or amino acids, respectively, compared to the naturally occurring (wild-type) nucleic acid or protein "reference" scaffold. A substitution of an amino acid of the naturally occurring (wild-type) nucleic acid or protein is preferred. The terms "reference", "reference sequence" and "wild type sequence" are used interchangeably herein.

The present disclosure also contemplates optimized variants of the lipocalin muteins specifically disclosed herein. Once a lipocalin mutein with affinity to a given target has been selected, it is possible to subject the mutein to further mutagenesis in order to subsequently select variants of even higher affinity or variants with improved properties such as higher thermostability, improved serum stability, thermodynamic stability, improved solubility, improved monomeric behavior, improved resistance against thermal denaturation, chemical denaturation, proteolysis, or detergents etc. This further mutagenesis, which in case of aiming at higher affinity can be considered as in vitro "affinity maturation", can be achieved by site specific mutation based on rational design or a random mutation. Another possible approach for obtaining a higher affinity or improved properties is the use of error-prone PCR, which results in point mutations over a selected range of sequence positions of the lipocalin mutein. The error-prone PCR can be carried out in accordance with any known protocol such as the one described by Zaccolo et al. (1996) J. Mol. Biol. 255, 589-603. Other methods of random mutagenesis suitable for such purposes include random insertion/deletion (RID) mutagenesis as described by Murakami, H et al. (2002) Nat. Biotechnol. 20, 76-81 or nonhomologous random recombination (NRR) as described by Bittker, J. A et al. (2002) Nat. Biotechnol. 20, 1024-1029. If desired, affinity maturation can also be carried out according to the procedure described in WO 00/75308 or Schlehuber, S. et al., (2000) J. Mol. Biol. 297, 1105-1120, where muteins of the bilin-binding protein having high affinity to digoxigenin were obtained.

A tear lipocalin mutein may be used for complex formation with IL 4 receptor alpha. The mutein may also be able to bind an immunogenic fragment of IL 4 receptor alpha. An immunogenic fragment of IL-4 receptor alpha is a fragment that has one or more epitopes, mimotopes or other antigenic determinants, and is thus capable of inducing an immune response or against which an antibody can be raised. The immunogenic fragment may include a single epitope or may have a plurality of epitopes. Since an antigen-presenting system, e.g. a carrier protein, may be used to provide the size required for recognition by an immune system, no particular size limitation applies to the immunogenic fragment. Hence, the immunogenic fragment may also be a "hapten", i.e. a fragment that need not be antigenic per se or may have low immunogenicity, in particular due to its small molecular weight and accordingly size. Typically an immunogenic fragment can, alone or when presented on a carrier, be bound by an immunoglobulin or by a T cell receptor (TCR) if presented by MHC molecules. An immunogenic fragment is typically, alone or when presented in the form of the antigen-presenting system, capable of inducing a humoral immune response and/or cellular immune response leading for instance to the activation of B- and/or T-lymphocytes.

One target of the lipocalin mutein used in the present disclosure is the alpha chain of the interleukin-4 receptor (officially known as Interleukin-4 receptor subunit alpha, Uniprot #P24394, SEQ ID NO: 12), a transmembrane protein, which contains an extracellular domain of 207 amino acids. A secreted form of the extracellular domain exists, sIL-4R alpha, which is also known as CD124 and capable of blocking IL-4 activities. A lipocalin mutein of the disclosure may be able to bind sIL-4 receptor alpha as well as any portion of the extracellular domain of IL-4 receptor alpha.

The present disclosure also relates to nucleic acid molecules (DNA and RNA) that include nucleotide sequences coding for lipocalin muteins as described herein. Since the degeneracy of the genetic code permits substitutions of certain codons by other codons specifying the same amino acid, the disclosure is not limited to a specific nucleic acid molecule encoding a lipocalin mutein of the disclosure but encompasses all nucleic acid molecules that include nucleotide sequences encoding a functional mutein.

The disclosed nucleic acid molecules can also be part of a vector or any other kind of cloning vehicle, such as a plasmid, a phagemid, a phage, a baculovirus, a cosmid or an artificial chromosome. In one embodiment, the nucleic acid molecule is included in a phasmid.

In some disclosed tear lipocalin muteins, the naturally occurring disulfide bond between Cys 61 and Cys 153 is removed. Accordingly, such muteins (or any other tear lipocalin mutein that does not include an intramolecular disulfide bond) can be produced in a cell compartment having a reducing redox milieu, for example, in the cytoplasma of Gram-negative bacteria. In case a lipocalin mutein of the disclosure includes intramolecular disulfide bonds, it may be desired to direct the nascent polypeptide to a cell compartment having an oxidizing redox milieu using an appropriate signal sequence. Such an oxidizing environment may be provided by the periplasm of Gram-negative bacteria such as *E. coli*, in the extracellular milieu of Gram-positive bacteria or in the lumen of the endoplasmatic reticulum of eukaryotic cells and usually favors the formation of structural disulfide bonds. It is, however, also possible to produce a lipocalin mutein of the disclosure in the cytosol of a host cell, such as *E. coli*. In this case, the polypeptide can either be directly obtained in a soluble and folded state or recovered in form of inclusion bodies, followed by renaturation in vitro. A further option is the use of specific host strains having an oxidizing intracellular milieu, which may thus allow the formation of disulfide bonds in the cytosol (Venturi M, et al. (2002) J. Mol. Biol. 315, 1-8).

The disclosure also relates to a composition, which includes at least one lipocalin mutein of the disclosure or a fragment or variant thereof or a fusion protein or conjugate thereof, and a pharmaceutically acceptable formulation (e.g. combination of buffer/salt/excipient), wherein the said composition may be administered to a subject in need thereof at a dosage level selected from the group consisting of: 0.06-600 mg, 0.06-100 mg, 0.3-10 mg, 1-3 mg.

In some embodiments, a composition of the present disclosure can be administered via any parenteral or non-parenteral (enteral) route that is therapeutically effective for proteinaceous drugs. Parenteral application methods include, for example, intracutaneous, subcutaneous, intramuscular, intratracheal, intranasal, intravitreal or intravenous injection and infusion techniques, e.g. in the form of injection solutions, infusion solutions or tinctures, as well as aerosol installation and inhalation, e.g. in the form of aerosol mixtures, sprays, mist or powders.

In some embodiments, local administration of the composition to the lung is preferred. A preferred route of local administration to the lung is via aerosol inhalation. An overview about pulmonary drug delivery, i.e. either via inhalation of aerosols (which can also be used in intranasal administration) or intratracheal instillation is given by Patton, J. S., et al. (2004) Proc. Amer. Thoracic Soc., 1, 338-344, for example). Non-parenteral delivery modes are, for instance, orally, e.g. in the form of pills, tablets, capsules, solutions or suspensions, or rectally, e.g. in the form of suppositories. In some embodiments, a lipocalin mutein of the disclosure can also be administered systemically or topically in formulations containing conventional non-toxic pharmaceutically acceptable excipients or carriers, additives and vehicles as desired. For administration of a lipocalin mutein of the disclosure via inhalation, the mutein may be present in a powder formulation together with an additional phase. The micronized powder of the lipocalin mutein may be mixed with a carrier material, for example lactose, dextrose, maltose, trehalose, as described in the patent specification WO96/02231, or the article of P. Lucas, K. Anderson, J. N. Staniforth, Protein deposition from dry powder inhalers, Pharmaceutical Research, Vol. 15, April 1988, pages 562-569. Alternatively, for inhalation purposes solid pharmaceutical preparations as described in US patent applications 2005/0014677 and 2009/0142407 may be used.

Therefore, a composition of the disclosure may comprise a lipocalin mutein of the disclosure as well as one of the disclosed formulations.

The dosage of the composition applied may vary within wide limits to achieve the desired preventive effect or therapeutic response. It will, for instance, depend on the affinity of the lipocalin mutein therein for a chosen ligand as well as on the half-life of the complex between the lipocalin mutein and the ligand in vivo. Further, the optimal dosage will depend on the biodistribution of the lipocalin mutein or a fragment or variant thereof or its fusion protein or its conjugate, the mode of administration, the severity of the disease/disorder being treated as well as the medical condition of the patient.

In some embodiments, the present disclosure provides a method of treating a subject in need thereof, comprising administering to the said subject a pharmaceutical composition via nebulization, wherein the pharmaceutical composition comprising at least an IL-4RA antagonist, or a fragment or variant thereof or a fusion protein or conjugate thereof and a suitable solution.

In various preferred embodiments, a pharmaceutically acceptable formulation of the disclosure can be a formulation for nebulization, for example a solution that can maintain the functional and structural integrity of the antagonist, or a fragment or variant thereof or a fusion protein or conjugate thereof, upon and after nebulization (e.g. remained monomeric and fully functionally active) and/or, can, in combination with the employed nebulizer, generates droplets of the desired size range. In this regard, as an exemplary illustration, the present disclosure teaches: the antagonist, for example, a lipocalin mutein of the disclosure, can be formulated as a solution comprising, e.g. 0.01 mg to 100 mg of the antagonist or a fragment or variant thereof or a fusion protein or conjugate thereof per 1 ml of a saline having a pH adjusted to between 5.5 and 8.0, an osmolality value between about 150 and 550 mOsm/kg, an ion concentration between about 31 and 300 mM of chloride as a permeant anion, and/or a viscosity smaller than 1.5 cp. Preferably, the formulated solution has a concentration of the antagonist or a fragment or variant thereof or a fusion protein or conjugate thereof at a level selected from the group consisting of: 0.05 mg/ml to 50 mg/ml, 0.1 mg/ml to 50 mg/ml, 0.05 mg/ml to 25 mg/ml, 0.1 mg/ml to 25 mg/ml, 0.05 mg/ml to 15 mg/ml, 0.1 mg/ml to 15 mg/ml, 0.05 mg/ml to 10 mg/ml and 0.1 mg/ml to 10 mg/ml. In one further preferred embodiment, the disclosed saline has an adjusted pH selected from the group consisting of between 5.5 and 8.0, between 6.0 and 8.0, between 6.0 and 7.5, between 5.5 and 7.5, between 6.0 and 7.0 and between 6.5 and 7.5; and/or an osmolality value selected from the group consisting of: between about 150 and 550 mOsm/L, between about 150 and 500 mOsm/L, between about 200 and 550 mOsm/L, between about 200 and 500 mOsm/L, between about 200 and 450 mOsm/L and between about 150 and 450 mOsm/L, Osmolarity is the measure of solute concentration, defined as the number of osmoles (Osm) of solute per liter (L) of solution, e.g. osmol/L or Osm/L; and/or an ion concentration of chloride as a permeant anion from the group consisting of between 31 and 300 mM, between 50 and 200 mM, between 50 and 300 mM, between 50 and 150 mM, 100 and 200 mM, between 100 and 300 mM, between 100 and 250 mM, between 150 and 250 mM, between 150 and 300 mM and between 200 and 300 mM.

Further preferably, the disclosed saline has a viscosity selected from the group consisting of between 0 and 1.5 cp, between 0 and 1.0 cp, 0 and 0.5 cp, between 0.5 and 1.0 cp, between 0.5 and 1.5 cp and between 1.0 and 1.5 cp.

In some further embodiments, the aqueous solution of the antagonist, for example, a lipocalin mutein of the disclosure, can be nebulized with an electronic nebulizer, jet, ultrasonic, or vibrating perforated membrane, e.g. the PARI eFlow or Aeroneb vibrating mesh nebulizer. In one preferred embodiment, the solution is nebulized into an aerosol having a mass median aerodynamic diameter (MMAD) between 1 μm and 10 μm, for electronic nebulizer, jet, ultrasonic, or vibrating perforated membrane, 2 times daily, and the said nebulizer is able to aerosolize the resulted solution into particles of required sizes (the aerosols) in a time period from about 1 to about 5 minutes. In some still further embodiment, any one of said aerosols may have a mass median aerodynamic diameter (MMAD) selected from the group consisting of between 1 μm to 10 μm, between 2 μm to 8 μm, between 2 μm to 5 μm, between 1.5 μm to 4 μm, between 3 μm to 4.5 μm and between 2.5 μm to 3.5 μm.

In some embodiments, the disclosure provides a method of delivery by inhalation, within 1-3 minutes, preferably 1-2 minutes, of efficacious amount of a pharmaceutical composition of the disclosure, comprising a disclosed nebulization formulation, to a subject in need thereof. In some further embodiments, said delivery by inhalation is locally to the lung.

In some other embodiments, therefore, the disclosure provides an efficacious, safe, nonirritating, physiologically acceptable and compatible solution suitable for being used in a method of the disclosure comprising administering a disclosed pharmaceutical composition to a subject in need thereof.

In some other embodiments, the disclosure provides use the solution for delivering a pharmaceutical composition of the disclosure to a subject in need thereof as aerosol, for example, by inhalation.

When used herein, "IL-4RA antagonist" means a polypeptide or protein that binds to IL-4RA with detectable binding affinity and/or is capable of inhibiting IL-4 and/or IL-13 from binding to their respective receptors. As used herein, "detectable affinity" means the ability to bind to a selected target with an affinity constant of generally at least about $10^{-5}$ M. Lower affinities are generally no longer measurable with common methods such as ELISA and therefore of secondary importance. For example, binding affinities of muteins according to the disclosure may in some embodiments be of a $K_D$ below 800 nM, in some embodiments be of a $K_D$ below 30 nM and in some embodiments about 50 picomolar (pM) or below In some embodiments, a lipocalin mutein of the present disclosure can be used to treat any disease or disorder in which the IL-4 expression and/or IL-13 expression contributes or is related to disease pathogenesis or aggravation. In some embodiments, a lipocalin mutein of the present disclosure can be used to treat any disease or disorder that is improved, ameliorated or inhibited by removal, inhibition or reduction of the IL-4 activity and/or IL-13 activity. As an illustrative example, the mutein or pharmaceutical composition containing the same may be utilized in a method of treating a disease or disorder associated with an increase of the Th2 immune response. Such disease or disorder may, for example, also be associated with an allergic reaction or an allergic inflammation. In some further embodiments, such disease or disorder may be allergic asthma, rhinitis, conjunctivitis or dermatitis (cf. Hage et al. (1999) Cell, 97, 271-281, or Mueller et al. (2002) Biochemica et Biophysica Acta, 237-250).

The term "fragment" as used in the present disclosure in connection with the tear lipocalin muteins of the disclosure relates to proteins or peptides derived from full-length mature human tear lipocalin that are N-terminally and/or C-terminally shortened, i.e. lacking at least one of the N-terminal and/or C-terminal amino acids. Such fragments comprise preferably at least 10, more preferably 20, most preferably 30 or more consecutive amino acids of the primary sequence of mature human tear lipocalin and are usually detectable in an immunoassay of mature human tear lipocalin.

The term "variant" as used in the present disclosure relates to derivatives of a protein or peptide (e.g. a tear lipocalin mutein of the disclosure) that comprise modifications of the amino acid sequence, for example by substitution, deletion, insertion or chemical modification. Preferably, such modifications do not reduce the functionality of the protein or peptide. Such variants include proteins, wherein one or more amino acids have been replaced by their respective D-stereoisomers or by amino acids other than the naturally occurring 20 amino acids, such as, for example, ornithine, hydroxyproline, citrulline, homoserine, hydroxylysine, norvaline. However, such substitutions may also be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan.

The term "position" when used in accordance with the disclosure means the position of either an amino acid within an amino acid sequence depicted herein or the position of a nucleotide within a nucleic acid sequence depicted herein. The term "corresponding" as used herein also includes that a position is not only determined by the number of the preceding nucleotides/amino acids. Accordingly, the position of a given amino acid in accordance with the disclosure which may be substituted may very due to deletion or addition of amino acids elsewhere in a (mutant or wild-type) lipocalin. Similarly, the position of a given nucleotide in accordance with the present disclosure which may be substituted may vary due to deletions or additional nucleotides elsewhere in a mutein or wild type lipocalin 5'-untranslated region (UTR) including the promoter and/or any other regulatory sequences or gene (including exons and introns). Thus, under a "corresponding position" in accordance with the disclosure it is preferably to be understood that nucleotides/amino acids may differ in the indicated number but may still have similar neighbouring nucleotides/amino acids. Said nucleotides/amino acids which may be exchanged, deleted or added are also comprised by the term "corresponding position". Specifically, in order to determine whether an amino acid residue of the amino acid sequence of a lipocalin (mutein) different from a wild-type lipocalin corresponds to a certain position in the amino acid sequence of a wild-type lipocalin, a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, a wild-type lipocalin can serve as "subject sequence" or "reference sequence", while the amino acid sequence of a lipocalin different from the wild-type lipocalin described herein serves as "query sequence". The terms "reference sequence" and "wild type sequence" are used interchangeably herein.

As used herein, the singular forms "a", "an", and "the", include plural references unless the context clearly indicates otherwise. Thus, for example, reference to "a lipocalin mutein" includes one or more lipocalin muteins.

Unless otherwise indicated, the term "at least" preceding a series of elements is to be understood to refer to every element in the series. Those skilled in the art will recognize, or be able to ascertain using no more than routine experimentation, many equivalents to the specific embodiments of the disclosure described herein. Such equivalents are intended to be encompassed by the present disclosure.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "having".

When used herein "consisting of" excludes any element, step, or ingredient not specified in the claim element. When used herein, "consisting essentially of" does not exclude materials or steps that do not materially affect the basic and novel characteristics of the claim.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or" as used herein.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the disclosure is not entitled to antedate such disclosure by virtue of prior disclosure.

EXAMPLES

Example 1

Inhibition of IL-4 and IL-13 Induced Stat6 Phosphorylation in TF-1 Cells by an IL-4 Receptor Alpha Antagonist TF-1 cells were incubated at 37° C. for 30 min with an IL-4 receptor alpha antagonist, a lipocalin mutein directed against the human IL-4 receptor alpha chain (SEQ ID NO: 6), before adding 10 nM IL-13 (FIG. 1a) or 0.1 nM IL-4 (FIG. 1b). Cells were fixed after incubation for 15 min at 37° C. with 1.6% PFA and permeabilized with 100% methanol prior to intracellular STAT6 staining with PE Mouse Anti- STAT6 (pY641)-BD 612701. The IL-4RA specific antibody MAB230 (R&D Systems) and the IL-4 double mutant IL-4 (R121D, Y124D) as described by Andrews et al. JI 2006 176:7456-7461 was used as positive control. In addition, the human tear lipocalin (SEQ ID NO: 1) and a mouse IgG2a antibody (mIgG2a, Ancell 281-010; Lot#171605) were used as negative controls. The results from the TF-1 Stat6 phosphorylation assay are depicted in FIG. 1 and show that the lipocalin mutein (SEQ ID NO: 6) is a potent antagonists of IL-4 as well as IL-13 as it relates to IL-4RA downstream signaling. The IL-4RA specific antibody MAB230 (R&D Systems) performs equally well. The IL-4 mutant to our surprise is significantly less effective in inhibiting both IL-4 and IL-13 induced Stat6 phosphorylation in TF-1 cells although functional antagonism had been described previously. The fast dissociation rate constant ($k_{off}$) of the IL-4 mutant (R121D, Y124D) compared to the lipocalin mutein (Table 1) might be the reason for this functional difference.

TABLE 1

| Test substance | KD | $k_{on}$ | $k_{off}$ |
|---|---|---|---|
| Lipocalin Mutein (SEQ ID NO: 6) | 23 pM | $4.1 \times 10^6$ M$^{-1}$s$^{-1}$ | $9.2 \times 10^{-5}$ s$^{-1}$ |
| IL-4 mutant (R121D, Y124D) | 154 pM | $1.9 \times 10^7$ M$^{-1}$s$^{-1}$ | $2.9 \times 10^{-3}$ s$^{-1}$ |

Example 2

Construction of Double Knock-in Mouse

Human IL-4 receptor alpha chain and IL-13 receptor alpha chain 1 knock-in mice were generated by replacing the mouse IL-4 receptor alpha chain gene and the IL-13 receptor alpha chain 1 gene with the respective human orthologue. Accordingly, the generated mice are so-called human IL-4 receptor alpha/human IL-13 receptor alpha chain 1 double knock-in mice which harbor the human instead of the mouse IL-4 receptor alpha and IL-13 receptor alpha chain 1 genes at the mouse orthologous gene locus.

The mice were generated as follows: The 70 kb mouse IL-13RA1 gene on chromosome X was deleted, generating a null allele in mouse embryonic stem cells. A segment of DNA carrying the human IL-13RA1 gene was introduced into the deleted locus. The human gene consists of a 95.7 kb fragment of the human X chromosome that contains not only the entire IL13RA gene but also ~11 kb of 5' inter-genic DNA and ~7 kb of DNA 3' of the 3'UTR. Implicit in this is the knowledge that this fragment of DNA will direct the expression of the human receptor. Mice carrying this alteration were generated from the modified ES cells. In a separate experiment, the 39 kb segment of DNA carrying the mouse IL-4RA gene was exchanged with the corresponding segment of 63 kb of DNA encoding human IL-4R, which is composed of IL-4R alpha and the common gamma chain, and again using a mouse line generated from the modified cells. The two Knock-in mouse lines were intercrossed to establish a mouse line homozygous for the humanized locus at both the IL-4R locus and the IL-13RA locus. The mice express the human proteins in the absence of the mouse proteins. The proper expression of the human Type I and Type II receptors was verified by demonstrating the response of immune cells to human IL4 and the response of airway epithelial cells to IL-13.

Example 3

Ex Vivo Analysis of Double Knock-in Mouse Splenocytes to Verify the Function of an IL-4 Receptor Alpha Antagonist on the IL-4 Type I Receptor Splenocytes were isolated from human IL-4 receptor alpha/human IL-13 receptor alpha chain 1 double knock-in mice by means and methods commonly known in the art. These splenocytes were stimulated with increasing concentrations of human IL-4 either in the absence or presence of an IL-4 receptor alpha antagonist, a lipocalin mutein directed against the human IL-4 receptor alpha chain (SEQ ID NO: 6). IL-4 effects phosphorylation of STAT6 via the IL-4 receptor complex. Thus, phosphorylation of STAT6 is therefore a read-out for IL-4 binding to its receptor. The human tear lipocalin (SEQ ID NO: 1) serves as a negative control.

Figure 2:
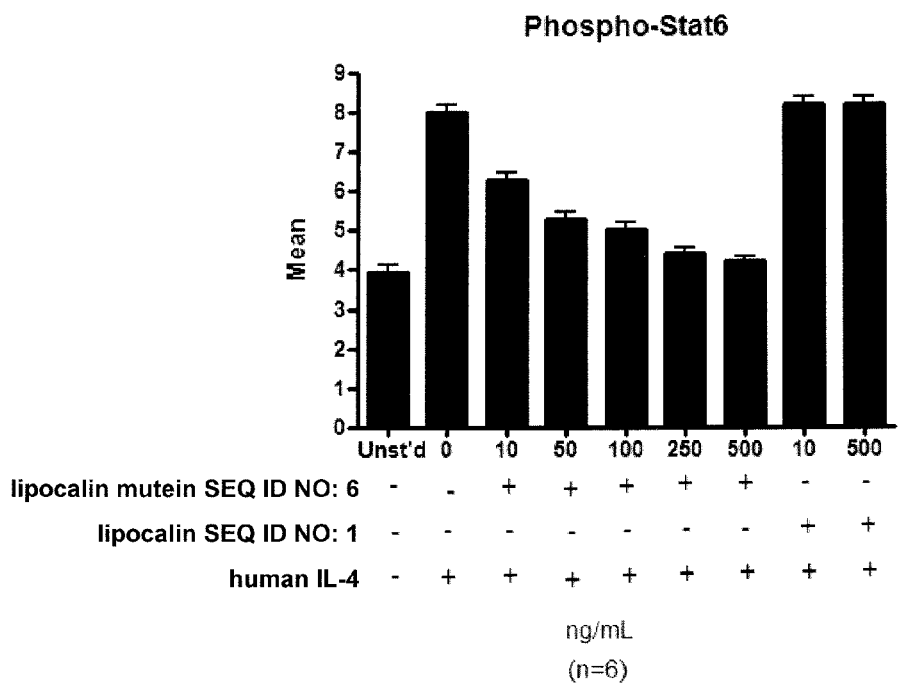
FIG. 2 depicts inhibition of human IL-4 induced STAT 6 phosphorylation (FACS-based assay) in human IL-4RA/IL-13RA1 (officially known as Interleukin-13 receptor subunit alpha-1, Uniprot #P78552, SEQ ID NO: 13) chain double knock-in mice by a lipocalin mutein of the disclosure.

In FIG. 2, it is shown that the lipocalin mutein (SEQ ID NO: 6) decreases, and thus neutralizes, action of IL-4 on the IL-4 type I receptor expressed on splenocytes, since STAT 6 phosphorylation in IL-4 stimulated splenocytes was equal to the level of unstimulated splenocytes.

Example 4

Administration of an IL-4 Receptor Alpha Antagonist to Double Knock-in Transgenic Mouse & Analysis of Eotaxin Levels The IL-13 induced airway inflammation model provided by Blanchard et al. (Clin Exp Allergy 2005, 35(8):1096-1103 was used to investigate the effect of an IL-4 receptor alpha antagonist, a lipocalin mutein directed against human IL-4 receptor alpha chain. In the model, 1 µg IL-13 is administered three times every 48 hours by intratracheal instillation.

Figure 3:
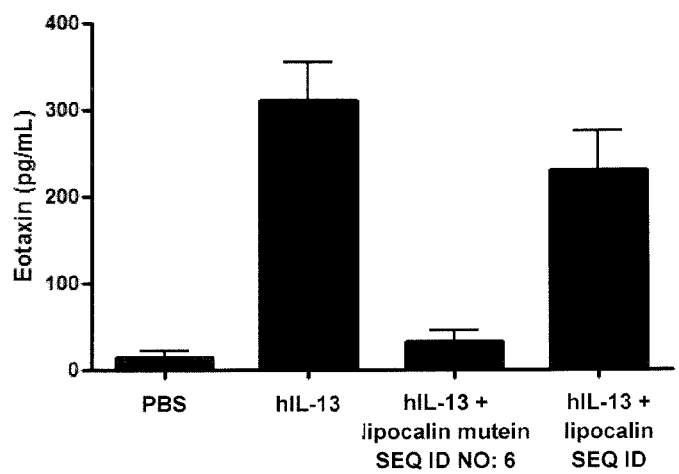
FIG. 3 depicts inhibition of human IL-13 induced eotaxin in lung tissue of human IL-4 receptor alpha/IL-13 receptor alpha 1 chain double knock-in mice by a lipocalin mutein of the disclosure.

Accordingly, as shown in FIG. 3, vehicle (phosphate buffered saline, thereafter referred as "PBS") or IL-13 (hIL-13) was administered to double knock-in transgenic mice, as group 1 (PBS) and group 2 (hIL-13), respectively, whereas group 3 (SEQ ID NO: 6/hIL-13) and group 4 (TLPC/hIL-13) received the lipocalin mutein (SEQ ID NO: 6) at a dose of 57 µg or the human tear lipocalin (SEQ ID NO: 1) as negative control at a dose of 57 µg, respectively, in addition to having received hIL-13.

Groups 2 and 3 contained 3 mice, while groups 1 and 4 contained 2 mice. Intratracheal dosing was done at 30 µl. IL-13, the lipocalin mutein (SEQ ID NO: 6) and the negative control were administered intratracheally and lung tissue homogenate was obtained with the aim of measuring eotaxin levels. Note that the lipocalin mutein and the negative control were administered 30 minutes prior to IL-13 administration.

When IL-13 is administered in this model, eotaxin levels increase e.g. 24 hours after the last IL-13 dose in group 4 compared to group1. Eotaxin is a potent eosinophil chemoattractant and thus a marker for inflammation, in particular allergic inflammation. It is shown in FIG. 3 that the lipocalin mutein (SEQ ID NO: 6) in group 4 effectively neutralizes the action of IL-13 on eotaxin induction in comparison to the negative control in group 3 (also cf. PBS group 1 and IL-13 alone group 2).

Example 5

Administration of an IL-4 Receptor Alpha Antagonist to Double Knock-in Transgenic Mouse & Analysis of mRNA Expression of Ccl11 (Eotaxin)

Figure 4:
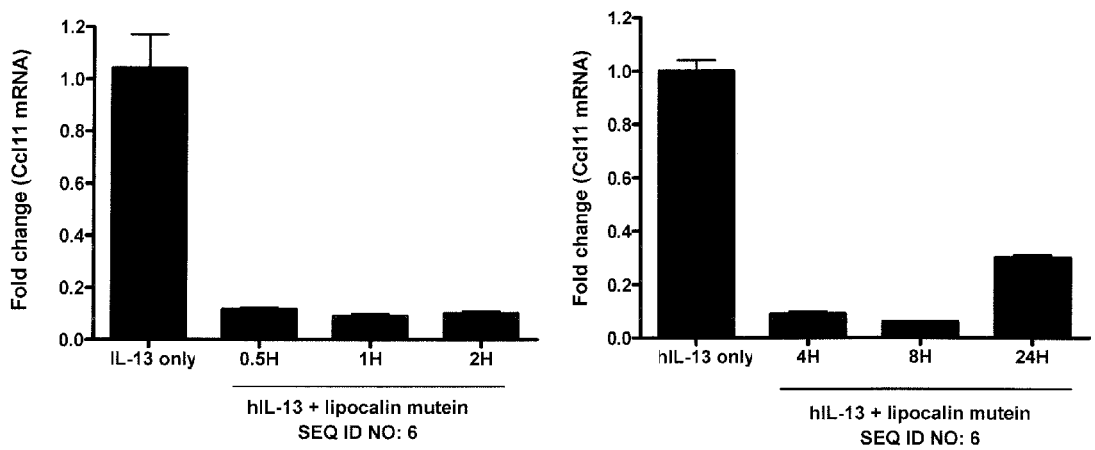
FIG. 4 depicts inhibition of human IL-13 induced eotaxin transcript in human IL-4 receptor alpha/IL-13 receptor alpha 1 chain double knock-in mice by a lipocalin mutein of the disclosure when administered at different time intervals (FIG. 4a) or different doses (FIG. 4b), prior to administration of human IL-13, as well as in comparison with an IL-4 mutant at different dose levels (FIG. 4c).
Figure 4:
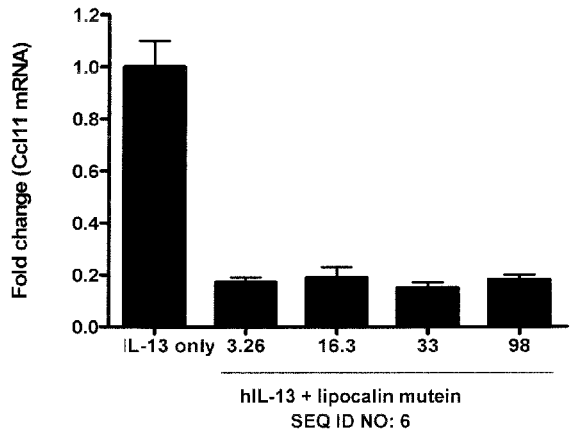

Administration of an IL-4 receptor alpha antagonist, a lipocalin mutein directed against human IL-4 receptor alpha chain (SEQ ID NO: 6), to human IL-4 receptor alpha/human IL-13 receptor alpha chain 1 double knock-in mice was done as described in Example 4 with the exception that 30 µl of IL-13 (Peprotech, 1 µg) was administered by intratracheal instillation only once. Each of the groups contained 3 human IL-4 receptor alpha/human IL-13 receptor alpha chain 1 double knock-in mice. Total RNA was isolated from lung homogenates 24 hours after the IL-13 dose and analyzed for mouse eotaxin expression by RT-PCR. mRNA expression in lung tissue after 24 h are normalized with 18S rRNA and the value for the 1 µg hIL13 mice set as 1. The lipocalin mutein (SEQ ID NO: 6) was also applied by intratracheal instillation with a volume of 30 µl either at a constant dose of 98 µg at different times prior to the IL-13 dose or at different amounts 30 minutes prior to the IL-13 dose. The IL-4 mutant (R121D, Y124D) was also applied by intratracheal instillation with a volume of 30 µl at different amounts 30 minutes prior to the IL-13 dose. The abbreviated IL-13 induced airway inflammation model (single IL-13 intratracheal administration) was used to assess the duration of the pharmacological response, dose dependency and comparable potency. In FIG. 4a, it can be seen that the lipocalin mutein (SEQ ID NO: 6) inhibited human IL-13 induced transcript Ccl11 (eotaxin) effectively for an extended period of time (FIG. 4a), while dose dependency of the pharmacological response was also demonstrated as shown in FIG. 4b. In addition, as can be seen in FIG. 4c, a favorable potency of the lipocalin mutein (SEQ ID NO: 6) was shown when compared side by side with the IL-4 mutant (FIG. 4c).

Example 6

Identification of Formulations Suitable for Nebulizing an IL-4 Receptor Alpha Antagonist Using the Pari eFlow Vibrating Mesh Nebulizer An IL-4 receptor alpha antagonist, an IL-4RA-specific lipocalin mutein (SEQ ID NO: 6), was nebulized with a Pari eFlow device at a concentration of 0.1 mg/ml in PBS containing either 0.01 or 0.05 polysorbate 20. The reservoir of the nebulizer was filled with 6 ml of the formulation and operated for approximately 15 minutes until half of the reservoir was nebulized. A shown in FIG. 5, the nebulized sample was collected with a glass vial fitted to the mouth piece of the nebulizer and analyzed by visual inspection to monitor visible particles, by light obscuration to monitor subvisible particles, by high pressure size exclusion chromatography (HP-SEC) to monitor soluble aggregates, by reverse phase SEC to monitor chemical modifications, by an IL-4RA binding ELISA to monitor functional activity and by laser diffraction to measure droplet size. Nebulization of the lipocalin mutein (SEQ ID NO: 6) in the chosen formulation did not lead to the generation of visible aggregate, subvisible particles. Both the nebulized protein and the protein remaining in the reservoir stayed monomeric and fully functionally active. Droplets with a median size of 5.5 µm were generated according to the specifications of the device. The concentration of polysorbate 20 in the formulation did not seem to influence the ability to nebulizer the mutein as none of the measured parameters were identical in formulations containing 0.01 or 0.05 polysorbate 20.

Example 7

Pharmacokinetic Properties and Biodistribution of an IL-4 Receptor Alpha Antagonist in Human IL-4RA/Human IL-13 Double Knock-in Mice after Intratracheal Instillation An IL-4 receptor alpha antagonist, the lipocalin mutein (SEQ ID NO: 6) was administered by intratracheal administration of 30 µl (98 µg) to human IL-4 receptor alpha/human IL-13 receptor alpha chain 1 double knock-in mice. Twenty animals were dosed and groups of 4 were sacrificed after 1, 4, 8, 16 and 24 hours. At the time of sacrifice, lungs were lavaged with 2×1 ml FACSflow fluid, Li-heparin plasma samples were drawn and the lungs were snap frozen in liquid nitrogen. The lung tissue was homogenated in 1.5 ml lysis buffer (one tablet of complete mini protease inhibitor cocktail tablets (Roche)/10 ml T-PER (Perbio)) using an IKA T10 basic Ultra-Turrax (S10N-5G) tissue homogenizer at 4° C. for 55 seconds. The homogenate was incubated on ice for 30-60 minutes and cleared by centrifugation with 10.000 g at 4° C. for 10 minutes. Total protein concentration was determined with a BCA kit (Pierce) according to the manufacturer's instructions and samples were diluted with PBS to a standard final protein concentration of 1 mg/ml prior to storage of aliquots at −80° C. A quantitative Meso Scale Discovery ("MSD") based ELISA was used to measure the binding active concentrations of the lipocalin mutein (SEQ ID NO: 6) in lavage fluid, lung tissue and plasma at the different time points. Briefly, MSD plates were coated with neutravidin, 5 µg/ml in PBS over night at 4° C., washed with PBS/0.05% Tween20 and blocked with 3% BSA. Biotinylated human IL-4RA at a concentration of 2.5 µg/ml in PBS/0.1% Tween20 was added to capture the lipocalin mutein from the different matrixes and the bound mutein was detected with a tear lipocalin specific rabbit polyclonal antibody (preparation: TLPC-Mix4666 Ab, Pieris, PL#684) and an anti-rabbit IgG Sulfo-Tag antibody (Meso Scale Discovery, 0.5 µg/ml) in PBS/0.5% Tween20/ 0.5% BSA. The assay exhibited in all three matrixes a linear range from 75 pg/ml to 6 ng/ml while QC samples had a recovery between 80-120%. For calculations of concentrations and total amounts a total plasma volume of 900 µl per mouse was assumed. The dilution factor used to standardize the lung homogenate to 1 mg/ml total protein concentration measured by the BCA kit was taking into account when the total amount of lipocalin mutein per lung was calculated based on the measured concentration in the standardized total lung homogenate and its volume of 1.5 ml lysis buffer and measured weight of the lungs. The total amount of the lipocalin mutein in bronchoalveolar lavage fluid (thereafter "BALF") was based on the amount recovered in 2 ml lavage fluid.

Figure 6:
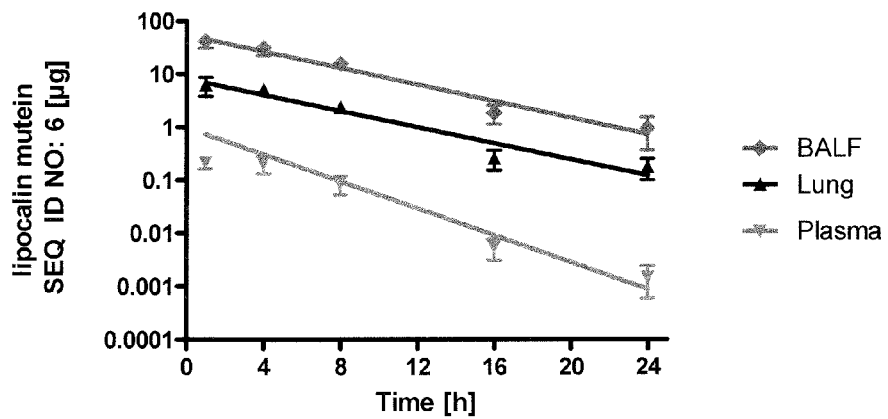
FIG. 6 depicts the pharmacokinetic properties and biodistribution of a lipocalin mutein of the disclosure in human IL-4RA/human IL-13 double knock-in mice after intratracheal instillation.
Figure 6:
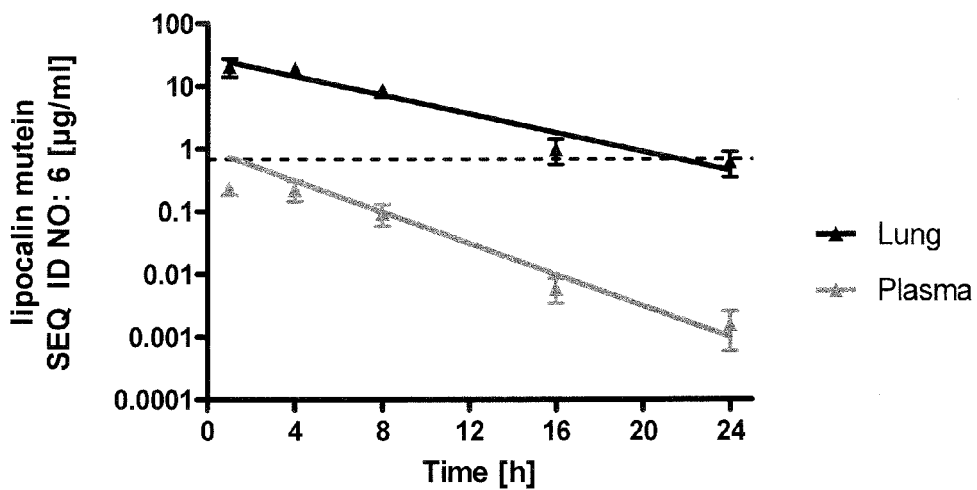

It can be seen in FIG. 6a that 43% of the administered dose could be recovered in the BALF, 6% in the lung tissue and 0.2% in plasma 1 hour after intratracheal administration. A terminal half-life of 3.7, 3.9 and 2.7 hours was determined in the BALF, lung tissue and plasma, respectively. Furthermore, it can be seen in FIG. 6b that the calculated lung tissue concentrations in human IL-4RA/human IL-13 double knock-in mice were maintained above 0.7 µg/ml after intratracheal instillation of 98 µg of the lipocalin mutein for approximately 20 hours which is in line with the observations shown in FIG. 4a. The 0.7 μg/ml concentration corresponds to the highest $IC_{90}$ value of the lipocalin mutein observed in different in vitro potency assays. Furthermore, FIG. 6b also shows that the plasma concentrations and therefore systemic exposure were 100 fold lower compared to the concentrations seen in the lung tissue.

Example 8

Inhibition of IL-13 Induced Goblet Cell Metaplasia in Human Airway Epithelium Air-Liquid-Interface Culture System by an IL-4 Receptor Alpha Antagonist Goblet cell metaplasia is a common feature of several respiratory diseases including Asthma. Therefore, the ability of an IL-4 receptor alpha antagonist, the lipocalin mutein (SEQ ID NO: 6), to prevent goblet cell metaplasia in an in vitro model based on MucilAir™ (Epithelix) was assessed. MucilAir™, an air-liquid interface culture system with human airway epithelium reconstituted in vitro using primary human cells was treated every two days with human IL-13 at 0.3 to 30 ng/ml. By in-situ Alcian blue staining, as well as histological analysis, it was demonstrated that MucilAir™ showed an increased goblet cell density after 14 days of treatment, in a dose dependent manner. Therefore, the inhibitory effect of the lipocalin mutein on goblet cell metaplasia was tested by comparing continuous exposure of MucilAir™ to 10 ng/ml human IL-13 for 14 days as positive control and to IL-13+ different concentrations (as shown in FIG. 7a) of the lipocalin mutein (SEQ ID NO: 6), the IL-4 mutant (R121D, Y124D) and an anti-IL-4RA monoclonal antibody (the light and heavy chain variable region are shown in SEQ D NOs: 14 and 15), respectively, and when compared to MucilAir™ cultured for 14 days without IL-13 as negative control. The Alcain blue stain, which stains acid mucopolysacharides and glycosaminoglycans in blue to bluish-green, was added to the apical surface for an in-situ stain and pictures from stained cells were taken under a phase contrast microscope for image analysis. The percentage of the Alcain blue positive cells was quantified by the public domain Java image processing program ImageJ and expressed as area ratio of Alcain blue area/total image area. Histological analysis has been performed by a platform at the Geneva University according to standard protocol. In addition, eotaxin-3, an IL-13 induced chemokine, was measured in the basal medium on day 14 using a commercially available ultrasensitive eotaxin-3 Kit from Meso Scale Discovery according to the manufacturer's instruction.

In FIG. 7a and FIG. 7b, it can be seen that the lipocalin mutein (SEQ ID NO: 6) was able to block IL-13 induced goblet cell metaplasia in the MucilAir culture system completely in a dose dependent manner. The level of Alcain blue area ratio was reduced to background (the ratio of the negative control having no IL-13) by the lipocalin mutein as well as the anti-IL-4RA monoclonal antibody but not by the IL-4 mutant (R121D, Y124D), while the human tear lipocalin (SEQ ID NO: 1) exhibited similar staining as the positive control (only having IL-13). Similar results were obtained for eotaxin-3 (secreted into the basal culture media) as seen in FIG. 7d. Exemplary Alcain blue/Neutral red stained paraffin sections of day 14 cultures with and without IL-13 as shown in FIG. 7c displayed the impact of IL-13 on human airway epithelium in the air-liquid-interface culture system.

The invention has industrial applications in connection with treatment of diseases and/or conditions in which the IL4/IL13 pathway contributes to disease pathogenesis, e.g. diseases and/or conditions associated with an increase of the Th2 immune response. The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention. The invention has been described broadly and generically herein. All patents, patent applications, text books and peer-reviewed publications described herein are hereby incorporated by reference in their entirety. Furthermore, where a definition or use of a term in a reference, which is incorporated by reference herein is inconsistent or contrary to the definition of that term provided herein, the definition of that term provided herein applies and the definition of that term in the reference does not apply. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group. Further embodiments of the invention will become apparent from the following claims.

The invention claimed is:

1. A method of treating or ameliorating a lung disorder that is related to the immune system, comprising administering to a subject in need thereof a human tear lipocalin mutein or a fusion protein, conjugate or composition thereof that is capable of inhibiting IL-4 and/or IL-13 from binding to their respective receptors, wherein said lipocalin mutein is capable of exhibiting in vivo therapeutic activity in the subject, wherein said lipocalin mutein has at least 75% sequence identity to the amino acid sequence of mature human tear lipocalin (SEQ ID NO: 1), wherein said lipocalin mutein has the following amino acid residues at amino acid positions corresponding to numbering of amino acids positions of mature human tear lipocalin (SEQ ID NO: 1): Ser at amino acid position 26, Arg at amino acid position 27, Cys at amino acid position 28, Arg at amino acid position 30, Ala at amino acid position 31, Val at amino acid position 32, Tyr at amino acid position 33, Asn at amino acid position 34, Phe at amino acid position 53, Ala at amino acid position 55, Gln at amino acid position 56, Arg at amino acid position 57, Lys at amino acid position 58, Trp at amino acid position 61, Lys at amino acid position 63, Tyr at amino acid position 64, Leu at amino acid position 66, Ser at amino acid position 80, Arg at amino acid position 83, Leu at amino acid position 104, Cys at amino acid position 105, Pro at amino acid position 106, and Gln at amino acid position 108.

2. The method of claim 1, wherein said lipocalin mutein is capable of disrupting downstream signaling and/or cellular responses induced by IL-4 and/or IL-13.

3. The method of claim 1, wherein said lipocalin mutein has the amino acid sequence as set forth in SEQ ID NO: 6.

4. The method of claim 1, wherein said lipocalin mutein is capable of inhibiting in vivo human IL-13 induced transcript Ccl11 (eotaxin).

5. The method of claim 1, wherein said lipocalin mutein is more potent than an IL-4 mutant (R121D, Y124D) when inhibiting human IL-13 induced transcript Ccl11 (eotaxin) in vivo.

6. The method of claim 1, wherein said lipocalin mutein is capable of exhibiting a functional activity as good as an anti-IL-4RA monoclonal antibody AMG 317 having the variable light and heavy chain sequence as shown in SEQ ID NO: 14 and 15, respectively, wherein said lipocalin mutein is capable of inhibiting IL-13-induced goblet cell metaplasia as good as the anti-IL-4RA monoclonal antibody.

7. The method of claim 1, wherein said lipocalin mutein, fusion protein, conjugate or composition is locally administered to the lung.

8. The method of claim 7, wherein said lipocalin mutein, fusion protein, conjugate or composition is administered via aerosol inhalation.

9. The method of claim 1, wherein said lipocalin mutein, fusion protein, conjugate or composition is administered to a subject in need thereof at a frequency selected from the group consisting of: up to four times daily, up to three times daily, up to twice daily, up to once daily, up to once every other day, up to once every third day, up to once every week, and up to once every other week.

10. The method of claim 1, wherein said lipocalin mutein, fusion protein, conjugate or composition is administered to a subject in need thereof every time at a dosage level selected from the group consisting of: 0.06-600 mg, 0.06-100 mg, 0.3-10 mg, and 1-3 mg.

11. The method of claim 1, wherein said disorder is associated with an increase of the Th2 immune response, an allergic reaction, an allergic inflammation, a mucus production, or a mucus secretion.

12. The method of claim 1, wherein the composition further comprises a pharmaceutically acceptable formulation.

13. The method of claim 1, wherein said composition further comprises an anti-allergic medicament, an anti-allergic inflammation medicament and/or an anti-mucus medicament.

14. The method of claim 1, wherein said lipocalin mutein is cross-reactive with marmoset IL-4RA and is not cross-reactive with mouse IL-4RA and/or cynomolgus IL-4RA.

15. The method of claim 1, wherein said lipocalin mutein is essentially not cross-reactive with IL-23 receptor alpha chain, type I cytokine receptor with fibronectin type III domain, IL-6 receptor or IL-18 receptor alpha chain.

16. The method of claim 1, wherein the disorder is selected from the group consisting of asthma, allergic asthma, rhinitis, lung fibrosis, and adult respiratory distress syndrome.

17. The method of claim 1, wherein said lipocalin mutein has at least 90% sequence identity to the amino acid sequence set forth in SEQ ID NO:6.

18. The method of claim 1, wherein said lipocalin mutein has at least 95% sequence identity to the amino acid sequence set forth in SEQ ID NO:6.

19. The method of claim 3, wherein the disorder is selected from the group consisting of asthma, allergic asthma, rhinitis, lung fibrosis, and adult respiratory distress syndrome.

20. The method of claim 19, wherein the disorder is asthma.

* * * * *

SEQUENCE LISTING

```
<160> NUMBER OF SEQ ID NOS: 15

<210> SEQ ID NO 1
<211> LENGTH: 158
<212> TYPE: PRT
<213> ORGANISM: Homo sapiens
<220> FEATURE:
<223> OTHER INFORMATION: mature human tear lipocalin

<400> SEQUENCE: 1
```

```
His His Leu Leu Ala Ser Asp Glu Glu Ile Gln Asp Val Ser Gly Thr
1               5                   10                  15

Trp Tyr Leu Lys Ala Met Thr Val Asp Arg Glu Phe Pro Glu Met Asn
            20                  25                  30

Leu Glu Ser Val Thr Pro Met Thr Leu Thr Thr Leu Glu Gly Gly Asn
        35                  40                  45

Leu Glu Ala Lys Val Thr Met Leu Ile Ser Gly Arg Cys Gln Glu Val
    50                  55                  60

Lys Ala Val Leu Glu Lys Thr Asp Glu Pro Gly Lys Tyr Thr Ala Asp
65                  70                  75                  80

Gly Gly Lys His Val Ala Tyr Ile Ile Arg Ser His Val Lys Asp His
                85                  90                  95

Tyr Ile Phe Tyr Cys Glu Gly Glu Leu His Gly Lys Pro Val Arg Gly
                100                 105                 110

Val Lys Leu Val Gly Arg Asp Pro Lys Asn Asn Leu Glu Ala Leu Glu
            115                 120                 125

Asp Phe Glu Lys Ala Ala Gly Ala Arg Gly Leu Ser Thr Glu Ser Ile
        130                 135                 140

Leu Ile Pro Arg Gln Ser Glu Thr Cys Ser Pro Gly Ser Asp
145                 150                 155

<210> SEQ ID NO 2
<211> LENGTH: 158
<212> TYPE: PRT
<213> ORGANISM: Artificial
<220> FEATURE:
<223> OTHER INFORMATION: Mutein 1 of human tear lipocalin with binding
      affinity for IL-4R alpha

<400> SEQUENCE: 2

His His Leu Leu Ala Ser Asp Glu Glu Ile Gln Asp Val Ser Gly Thr
1               5                   10                  15

Trp Tyr Leu Lys Ala Met Thr Val Asp Ser Arg Cys Pro Arg Ala Tyr
            20                  25                  30

Tyr Ser Ser Val Thr Pro Met Thr Leu Thr Thr Leu Glu Gly Gly Asn
        35                  40                  45

Leu Glu Ala Lys Phe Thr Ala Gln Arg Ser Gly Arg Trp Gln Glu Tyr
    50                  55                  60

Lys Leu Val Leu Glu Lys Thr Asp Glu Pro Gly Lys Tyr Thr Ala Ser
65                  70                  75                  80

Gly Gly Arg His Val Ala Tyr Ile Ile Arg Ser His Val Lys Asp His
                85                  90                  95

Tyr Ile Phe His Ser Glu Gly Leu Cys Pro Gly Gln Pro Val Pro Gly
                100                 105                 110

Val Trp Leu Val Gly Arg Asp Pro Lys Asn Asn Leu Glu Ala Leu Glu
            115                 120                 125

Asp Phe Glu Lys Ala Ala Gly Ala Arg Gly Leu Ser Thr Glu Ser Ile
        130                 135                 140

Leu Ile Pro Arg Gln Ser Glu Thr Ser Ser Pro Gly Ser Ala
145                 150                 155

<210> SEQ ID NO 3
<211> LENGTH: 158
<212> TYPE: PRT
<213> ORGANISM: Artificial
```

```
<220> FEATURE:
<223> OTHER INFORMATION: Mutein 2 of human tear lipocalin with binding
      affinity for IL-4R alpha

<400> SEQUENCE: 3

His His Leu Leu Ala Ser Asp Glu Glu Ile Gln Asp Val Ser Gly Thr
1               5                   10                  15

Trp Tyr Leu Lys Ala Met Thr Val Asp Ser Arg Cys Pro Arg Ala Tyr
            20                  25                  30

Tyr Glu Ser Val Thr Pro Met Thr Leu Thr Thr Leu Glu Gly Gly Asn
        35                  40                  45

Leu Glu Ala Lys Leu Thr Leu Gln Arg Lys Gly Arg Trp Gln Glu Met
    50                  55                  60

Lys Asp Val Leu Glu Lys Thr Asp Glu Pro Gly Lys Tyr Thr Ala Ser
65                  70                  75                  80

Gly Gly Arg His Val Ala Tyr Ile Ile Arg Ser His Val Lys Asp His
                85                  90                  95

Tyr Ile Phe His Ser Glu Gly Leu Cys Pro Gly Gln Pro Val Pro Gly
            100                 105                 110

Val Trp Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Ser Ser Pro Gly Ser Ala
145                 150                 155

<210> SEQ ID NO 4
<211> LENGTH: 158
<212> TYPE: PRT
<213> ORGANISM: Artificial
<220> FEATURE:
<223> OTHER INFORMATION: Mutein 3 of human tear lipocalin with binding
      affinity for IL-4R alpha

<400> SEQUENCE: 4

His His Leu Leu Ala Ser Asp Glu Glu Ile Gln Asp Val Ser Gly Thr
1               5                   10                  15

Trp Tyr Leu Lys Ala Met Thr Val Asp Pro Arg Cys Pro Arg Ala Tyr
            20                  25                  30

Tyr Ser Ser Val Thr Pro Met Thr Leu Thr Thr Leu Glu Gly Gly Asn
        35                  40                  45

Leu Glu Ala Lys Phe Thr Ala Gln Arg Ser Gly Arg Trp Gln Lys Tyr
    50                  55                  60

Lys Leu Val Leu Glu Lys Thr Asp Glu Pro Gly Lys Tyr Thr Ala Ser
65                  70                  75                  80

Gly Gly Arg His Val Ala Tyr Ile Ile Arg Ser His Val Lys Asp His
                85                  90                  95

Tyr Ile Phe His Ser Glu Gly Leu Cys Pro Gly Gln Pro Val Pro Gly
            100                 105                 110

Val Trp Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Ser Ser Pro Gly Ser Ala
145                 150                 155
```

```
<210> SEQ ID NO 5
<211> LENGTH: 158
<212> TYPE: PRT
<213> ORGANISM: Artificial
<220> FEATURE:
<223> OTHER INFORMATION: Mutein 4 of human tear lipocalin with binding
      affinity for IL-4R alpha

<400> SEQUENCE: 5

His His Leu Leu Ala Ser Asp Glu Glu Ile Gln Asp Val Ser Gly Thr
1               5                   10                  15

Trp Tyr Leu Lys Ala Met Thr Val Asp Leu Arg Cys Pro Arg Ala Tyr
            20                  25                  30

Tyr Trp Ser Val Thr Pro Met Thr Leu Thr Thr Leu Glu Gly Gly Asn
        35                  40                  45

Leu Glu Ala Lys Phe Thr Ala Leu Arg Ile Gly Arg Trp Gln Ser Tyr
    50                  55                  60

Lys Leu Val Leu Glu Lys Thr Asp Glu Pro Gly Lys Tyr Thr Ala Ser
65                  70                  75                  80

Gly Gly Arg His Val Ala Tyr Ile Ile Arg Ser His Val Lys Asp His
                85                  90                  95

Tyr Ile Phe His Ser Glu Gly Leu Cys Pro Gly Gln Pro Val Pro Gly
            100                 105                 110

Val Trp Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Ser Ser Pro Gly Ser Ala
145                 150                 155

<210> SEQ ID NO 6
<211> LENGTH: 158
<212> TYPE: PRT
<213> ORGANISM: Artificial
<220> FEATURE:
<223> OTHER INFORMATION: Mutein 5 of human tear lipocalin with binding
      affinity for IL-4R alpha

<400> SEQUENCE: 6

His His Leu Leu Ala Ser Asp Glu Glu Ile Gln Asp Val Ser Gly Thr
1               5                   10                  15

Trp Tyr Leu Lys Ala Met Thr Val Asp Ser Arg Cys Pro Arg Ala Val
            20                  25                  30

Tyr Asn Ser Val Thr Pro Met Thr Leu Thr Thr Leu Glu Gly Gly Asn
        35                  40                  45

Leu Glu Ala Lys Phe Thr Ala Gln Arg Lys Gly Arg Trp Gln Lys Tyr
    50                  55                  60

Lys Leu Val Leu Glu Lys Thr Asp Glu Pro Gly Lys Tyr Thr Ala Ser
65                  70                  75                  80

Gly Gly Arg His Val Ala Tyr Ile Ile Arg Ser His Val Lys Asp His
                85                  90                  95

Tyr Ile Phe His Ser Glu Gly Leu Cys Pro Gly Gln Pro Val Pro Gly
            100                 105                 110

Val Trp Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
    130                 135                 140
```

```
Leu Ile Pro Arg Gln Ser Glu Thr Ser Ser Pro Gly Ser Ala
145                 150                 155

<210> SEQ ID NO 7
<211> LENGTH: 158
<212> TYPE: PRT
<213> ORGANISM: Artificial
<220> FEATURE:
<223> OTHER INFORMATION: Mutein 6 of human tear lipocalin with binding
      affinity for IL-4R alpha

<400> SEQUENCE: 7

His His Leu Leu Ala Ser Asp Glu Glu Ile Gln Asp Val Ser Gly Thr
1               5                   10                  15

Trp Tyr Leu Lys Ala Met Thr Val Asp Ser Arg Cys Pro Arg Ala Tyr
            20                  25                  30

Tyr Val Ser Val Thr Pro Met Thr Leu Thr Thr Leu Glu Gly Gly Asn
        35                  40                  45

Leu Glu Ala Lys Phe Thr Ala Ala Arg Ile Gly Arg Trp Gln Ser Tyr
    50                  55                  60

Lys Leu Val Leu Glu Lys Thr Asp Glu Pro Gly Lys Tyr Thr Ala Ser
65                  70                  75                  80

Gly Gly Arg His Val Ala Tyr Ile Ile Arg Ser His Val Lys Asp His
                85                  90                  95

Tyr Ile Phe His Ser Glu Gly Leu Cys Pro Gly Gln Pro Val Pro Gly
            100                 105                 110

Val Trp Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Ser Ser Pro Gly Ser Ala
145                 150                 155

<210> SEQ ID NO 8
<211> LENGTH: 158
<212> TYPE: PRT
<213> ORGANISM: Artificial
<220> FEATURE:
<223> OTHER INFORMATION: Mutein 7 of human tear lipocalin with binding
      affinity for IL-4R alpha

<400> SEQUENCE: 8

His His Leu Leu Ala Ser Asp Glu Glu Ile Gln Asp Val Ser Gly Thr
1               5                   10                  15

Trp Tyr Leu Lys Ala Met Thr Val Asp Asn Arg Cys Pro Arg Ala Lys
            20                  25                  30

Tyr Asp Ser Val Thr Pro Met Thr Leu Thr Thr Leu Glu Gly Gly Asn
        35                  40                  45

Leu Glu Ala Lys Phe Thr Ala His Arg Arg Gly Arg Trp Gln Gln Tyr
    50                  55                  60

Lys Leu Val Leu Glu Lys Thr Asp Glu Pro Gly Lys Tyr Thr Ala Ser
65                  70                  75                  80

Gly Gly Arg His Val Ala Tyr Ile Ile Arg Ser His Val Lys Asp His
                85                  90                  95

Tyr Ile Phe His Ser Glu Gly Leu Cys Pro Gly Gln Pro Val Pro Gly
            100                 105                 110

Val Trp Leu Val Gly Arg Asp Pro Lys Asn Asn Leu Glu Ala Leu Glu
        115                 120                 125
```

```
Asp Phe Glu Lys Ala Ala Gly Ala Arg Gly Leu Ser Thr Glu Ser Ile
        130                 135                 140

Leu Ile Pro Arg Gln Ser Glu Thr Ser Ser Pro Gly Ser Ala
145                 150                 155

<210> SEQ ID NO 9
<211> LENGTH: 158
<212> TYPE: PRT
<213> ORGANISM: Artificial
<220> FEATURE:
<223> OTHER INFORMATION: Mutein 8 of human tear lipocalin with binding
      affinity for IL-4R alpha

<400> SEQUENCE: 9

His His Leu Leu Ala Ser Asp Glu Glu Ile Gln Asp Val Ser Gly Thr
1               5                   10                  15

Trp Tyr Leu Lys Ala Met Thr Val Asp Tyr Arg Cys Pro Arg Ala Tyr
            20                  25                  30

Tyr His Ser Val Thr Pro Met Thr Leu Thr Thr Leu Glu Gly Gly Asn
        35                  40                  45

Leu Glu Ala Lys Phe Thr Ala His Arg Ala Gly Arg Trp Gln Lys Tyr
50                  55                  60

Lys Leu Val Leu Glu Lys Thr Asp Glu Pro Gly Lys Tyr Thr Ala Ser
65                  70                  75                  80

Gly Gly Arg His Val Ala Tyr Ile Ile Arg Ser His Val Lys Asp His
                85                  90                  95

Tyr Ile Phe His Ser Glu Gly Leu Cys Pro Gly Gln Pro Val Pro Gly
            100                 105                 110

Val Trp Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Ser Ser Pro Gly Ser Ala
145                 150                 155

<210> SEQ ID NO 10
<211> LENGTH: 158
<212> TYPE: PRT
<213> ORGANISM: Artificial
<220> FEATURE:
<223> OTHER INFORMATION: Mutein 9 of human tear lipocalin with binding
      affinity for IL-4R alpha

<400> SEQUENCE: 10

His His Leu Leu Ala Ser Asp Glu Glu Ile Gln Asp Val Ser Gly Thr
1               5                   10                  15

Trp Tyr Leu Lys Ala Met Thr Val Asp Lys Arg Cys Pro Arg Ala Tyr
            20                  25                  30

Tyr Arg Ser Val Thr Pro Met Thr Leu Thr Thr Leu Glu Gly Gly Asn
        35                  40                  45

Leu Glu Ala Lys Phe Thr Ala Lys Arg Asn Gly Arg Trp Gln Pro Tyr
50                  55                  60

Lys Leu Val Leu Glu Lys Thr Asp Glu Pro Gly Lys Tyr Thr Ala Ser
65                  70                  75                  80

Gly Gly Arg His Val Ala Tyr Ile Ile Arg Ser His Val Lys Asp His
                85                  90                  95

Tyr Ile Phe His Ser Glu Gly Leu Cys Pro Gly Gln Pro Val Pro Gly
            100                 105                 110
```

Val Trp Leu Val Gly Arg Asp Pro Lys Asn Asn Leu Glu Ala Leu Glu
            115                 120                 125

Asp Phe Glu Lys Ala Ala Gly Ala Arg Gly Leu Ser Thr Glu Ser Ile
        130                 135                 140

Leu Ile Pro Arg Gln Ser Glu Thr Ser Ser Pro Gly Ser Ala
145                 150                 155

<210> SEQ ID NO 11
<211> LENGTH: 158
<212> TYPE: PRT
<213> ORGANISM: Artificial
<220> FEATURE:
<223> OTHER INFORMATION: Mutein 10 of human tear lipocalin with binding
      affinity for IL-4R alpha

<400> SEQUENCE: 11

His His Leu Leu Ala Ser Asp Glu Glu Ile Gln Asp Val Ser Gly Thr
1               5                   10                  15

Trp Tyr Leu Lys Ala Met Thr Val Asp Glu Arg Cys Pro Arg Ala His
            20                  25                  30

Tyr Gly Ser Val Thr Pro Met Thr Leu Thr Thr Leu Glu Gly Gly Asn
        35                  40                  45

Leu Glu Ala Lys Phe Thr Ala Met Arg Leu Gly Arg Trp Gln Lys Tyr
    50                  55                  60

Lys Leu Val Leu Glu Lys Thr Asp Glu Pro Gly Lys Tyr Thr Ala Ser
65                  70                  75                  80

Gly Gly Arg His Val Ala Tyr Ile Ile Arg Ser His Val Lys Asp His
                85                  90                  95

Tyr Ile Phe His Ser Glu Gly Leu Cys Pro Gly Gln Pro Val Pro Gly
            100                 105                 110

Val Trp Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Ser Ser Pro Gly Ser Ala
145                 150                 155

<210> SEQ ID NO 12
<211> LENGTH: 825
<212> TYPE: PRT
<213> ORGANISM: Homo sapiens
<220> FEATURE:
<223> OTHER INFORMATION: Human IL-4 receptor

<400> SEQUENCE: 12

Met Gly Trp Leu Cys Ser Gly Leu Leu Phe Pro Val Ser Cys Leu Val
1               5                   10                  15

Leu Leu Gln Val Ala Ser Ser Gly Asn Met Lys Val Leu Gln Glu Pro
            20                  25                  30

Thr Cys Val Ser Asp Tyr Met Ser Ile Ser Thr Cys Glu Trp Lys Met
        35                  40                  45

Asn Gly Pro Thr Asn Cys Ser Thr Glu Leu Arg Leu Leu Tyr Gln Leu
    50                  55                  60

Val Phe Leu Leu Ser Glu Ala His Thr Cys Ile Pro Glu Asn Asn Gly
65                  70                  75                  80

Gly Ala Gly Cys Val Cys His Leu Leu Met Asp Asp Val Val Ser Ala
                85                  90                  95

```
Asp Asn Tyr Thr Leu Asp Leu Trp Ala Gly Gln Gln Leu Leu Trp Lys
                100                 105                 110

Gly Ser Phe Lys Pro Ser Glu His Val Lys Pro Arg Ala Pro Gly Asn
            115                 120                 125

Leu Thr Val His Thr Asn Val Ser Asp Thr Leu Leu Leu Thr Trp Ser
        130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
                165                 170                 175

Val Thr Tyr Leu Glu Pro Ser Leu Arg Ile Ala Ala Ser Thr Leu Lys
            180                 185                 190

Ser Gly Ile Ser Tyr Arg Ala Arg Val Arg Ala Trp Ala Gln Cys Tyr
        195                 200                 205

Asn Thr Thr Trp Ser Glu Trp Ser Pro Ser Thr Lys Trp His Asn Ser
210                 215                 220

Tyr Arg Glu Pro Phe Glu Gln His Leu Leu Gly Val Ser Val Ser
225                 230                 235                 240

Cys Ile Val Ile Leu Ala Val Cys Leu Leu Cys Tyr Val Ser Ile Thr
            245                 250                 255

Lys Ile Lys Lys Glu Trp Trp Asp Gln Ile Pro Asn Pro Ala Arg Ser
            260                 265                 270

Arg Leu Val Ala Ile Ile Gln Asp Ala Gln Gly Ser Gln Trp Glu
            275                 280                 285

Lys Arg Ser Arg Gly Gln Glu Pro Ala Lys Cys Pro His Trp Lys Asn
290                 295                 300

Cys Leu Thr Lys Leu Leu Pro Cys Phe Leu Glu His Asn Met Lys Arg
305                 310                 315                 320

Asp Glu Asp Pro His Lys Ala Ala Lys Glu Met Pro Phe Gln Gly Ser
                325                 330                 335

Gly Lys Ser Ala Trp Cys Pro Val Glu Ile Ser Lys Thr Val Leu Trp
            340                 345                 350

Pro Glu Ser Ile Ser Val Val Arg Cys Val Glu Leu Phe Glu Ala Pro
            355                 360                 365

Val Glu Cys Glu Glu Glu Glu Val Glu Glu Lys Gly Ser Phe
370                 375                 380

Cys Ala Ser Pro Glu Ser Ser Arg Asp Asp Phe Gln Glu Gly Arg Glu
385                 390                 395                 400

Gly Ile Val Ala Arg Leu Thr Glu Ser Leu Phe Leu Asp Leu Leu Gly
            405                 410                 415

Glu Glu Asn Gly Gly Phe Cys Gln Gln Asp Met Gly Glu Ser Cys Leu
            420                 425                 430

Leu Pro Pro Ser Gly Ser Thr Ser Ala His Met Pro Trp Asp Glu Phe
        435                 440                 445

Pro Ser Ala Gly Pro Lys Glu Ala Pro Pro Trp Gly Lys Glu Gln Pro
    450                 455                 460

Leu His Leu Glu Pro Ser Pro Ala Ser Pro Thr Gln Ser Pro Asp
465                 470                 475                 480

Asn Leu Thr Cys Thr Glu Thr Pro Leu Val Ile Ala Gly Asn Pro Ala
                485                 490                 495

Tyr Arg Ser Phe Ser Asn Ser Leu Ser Gln Ser Pro Cys Pro Arg Glu
                500                 505                 510

Leu Gly Pro Asp Pro Leu Leu Ala Arg His Leu Glu Glu Val Glu Pro
```

```
            515                 520                 525
Glu Met Pro Cys Val Pro Gln Leu Ser Glu Pro Thr Thr Val Pro Gln
        530                 535                 540

Pro Glu Pro Glu Thr Trp Glu Gln Ile Leu Arg Arg Asn Val Leu Gln
545                 550                 555                 560

His Gly Ala Ala Ala Pro Val Ser Ala Pro Thr Ser Gly Tyr Gln
                565                 570                 575

Glu Phe Val His Ala Val Glu Gln Gly Gly Thr Gln Ala Ser Ala Val
                580                 585                 590

Val Gly Leu Gly Pro Pro Gly Glu Ala Gly Tyr Lys Ala Phe Ser Ser
            595                 600                 605

Leu Leu Ala Ser Ser Ala Val Ser Pro Glu Lys Cys Gly Phe Gly Ala
        610                 615                 620

Ser Ser Gly Glu Glu Gly Tyr Lys Pro Phe Gln Asp Leu Ile Pro Gly
625                 630                 635                 640

Cys Pro Gly Asp Pro Ala Pro Val Pro Val Pro Leu Phe Thr Phe Gly
                645                 650                 655

Leu Asp Arg Glu Pro Pro Arg Ser Pro Gln Ser Ser His Leu Pro Ser
                660                 665                 670

Ser Ser Pro Glu His Leu Gly Leu Glu Pro Gly Glu Lys Val Glu Asp
            675                 680                 685

Met Pro Lys Pro Pro Leu Pro Gln Glu Gln Ala Thr Asp Pro Leu Val
        690                 695                 700

Asp Ser Leu Gly Ser Gly Ile Val Tyr Ser Ala Leu Thr Cys His Leu
705                 710                 715                 720

Cys Gly His Leu Lys Gln Cys His Gly Gln Glu Asp Gly Gly Gln Thr
                725                 730                 735

Pro Val Met Ala Ser Pro Cys Cys Gly Cys Cys Cys Gly Asp Arg Ser
                740                 745                 750

Ser Pro Pro Thr Thr Pro Leu Arg Ala Pro Asp Pro Ser Pro Gly Gly
            755                 760                 765

Val Pro Leu Glu Ala Ser Leu Cys Pro Ala Ser Leu Ala Pro Ser Gly
        770                 775                 780

Ile Ser Glu Lys Ser Lys Ser Ser Ser Phe His Pro Ala Pro Gly
785                 790                 795                 800

Asn Ala Gln Ser Ser Ser Gln Thr Pro Lys Ile Val Asn Phe Val Ser
                805                 810                 815

Val Gly Pro Thr Tyr Met Arg Val Ser
            820                 825

<210> SEQ ID NO 13
<211> LENGTH: 427
<212> TYPE: PRT
<213> ORGANISM: Homo sapiens
<220> FEATURE:
<223> OTHER INFORMATION: human IL-13 receptor alpha 1

<400> SEQUENCE: 13

Met Glu Trp Pro Ala Arg Leu Cys Gly Leu Trp Ala Leu Leu Leu Cys
1               5                   10                  15

Ala Gly Gly Gly Gly Gly Gly Gly Ala Ala Pro Thr Glu Thr Gln
                20                  25                  30

Pro Pro Val Thr Asn Leu Ser Val Ser Val Glu Asn Leu Cys Thr Val
            35                  40                  45

Ile Trp Thr Trp Asn Pro Pro Glu Gly Ala Ser Ser Asn Cys Ser Leu
```

```
            50                  55                  60
Trp Tyr Phe Ser His Phe Gly Asp Lys Gln Asp Lys Ile Ala Pro
 65                  70                  75                  80

Glu Thr Arg Arg Ser Ile Glu Val Pro Leu Asn Glu Arg Ile Cys Leu
                 85                  90                  95

Gln Val Gly Ser Gln Cys Ser Thr Asn Glu Ser Glu Lys Pro Ser Ile
                100                 105                 110

Leu Val Glu Lys Cys Ile Ser Pro Pro Glu Gly Asp Pro Glu Ser Ala
                115                 120                 125

Val Thr Glu Leu Gln Cys Ile Trp His Asn Leu Ser Tyr Met Lys Cys
130                 135                 140

Ser Trp Leu Pro Gly Arg Asn Thr Ser Pro Asp Thr Asn Tyr Thr Leu
145                 150                 155                 160

Tyr Tyr Trp His Arg Ser Leu Glu Lys Ile His Gln Cys Glu Asn Ile
                165                 170                 175

Phe Arg Glu Gly Gln Tyr Phe Gly Cys Ser Phe Asp Leu Thr Lys Val
                180                 185                 190

Lys Asp Ser Ser Phe Glu Gln His Ser Val Gln Ile Met Val Lys Asp
                195                 200                 205

Asn Ala Gly Lys Ile Lys Pro Ser Phe Asn Ile Val Pro Leu Thr Ser
210                 215                 220

Arg Val Lys Pro Asp Pro Pro His Ile Lys Asn Leu Ser Phe His Asn
225                 230                 235                 240

Asp Asp Leu Tyr Val Gln Trp Glu Asn Pro Gln Asn Phe Ile Ser Arg
                245                 250                 255

Cys Leu Phe Tyr Glu Val Glu Val Asn Asn Ser Gln Thr Glu Thr His
                260                 265                 270

Asn Val Phe Tyr Val Gln Glu Ala Lys Cys Glu Asn Pro Glu Phe Glu
                275                 280                 285

Arg Asn Val Glu Asn Thr Ser Cys Phe Met Val Pro Gly Val Leu Pro
290                 295                 300

Asp Thr Leu Asn Thr Val Arg Ile Arg Val Lys Thr Asn Lys Leu Cys
305                 310                 315                 320

Tyr Glu Asp Asp Lys Leu Trp Ser Asn Trp Ser Gln Glu Met Ser Ile
                325                 330                 335

Gly Lys Lys Arg Asn Ser Thr Leu Tyr Ile Thr Met Leu Leu Ile Val
                340                 345                 350

Pro Val Ile Val Ala Gly Ala Ile Ile Val Leu Leu Leu Tyr Leu Lys
                355                 360                 365

Arg Leu Lys Ile Ile Ile Phe Pro Pro Ile Pro Asp Pro Gly Lys Ile
370                 375                 380

Phe Lys Glu Met Phe Gly Asp Gln Asn Asp Asp Thr Leu His Trp Lys
385                 390                 395                 400

Lys Tyr Asp Ile Tyr Glu Lys Gln Thr Lys Glu Glu Thr Asp Ser Val
                405                 410                 415

Val Leu Ile Glu Asn Leu Lys Lys Ala Ser Gln
                420                 425

<210> SEQ ID NO 14
<211> LENGTH: 109
<212> TYPE: PRT
<213> ORGANISM: human
<220> FEATURE:
<221> NAME/KEY: misc_feature
<222> LOCATION: (1)..(109)
```

```
<223> OTHER INFORMATION: 12B5 antibody variable light chain from
      WO 01/92340

<400> SEQUENCE: 14

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Phe Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65              70                  75                  80

Pro Glu Asp Phe Ala Val Tyr Tyr Cys Gln Gln Tyr Gly Ser Ser Pro
                85                  90                  95

Pro Trp Thr Phe Gly Gln Gly Thr Lys Val Glu Ile Lys
            100                 105

<210> SEQ ID NO 15
<211> LENGTH: 115
<212> TYPE: PRT
<213> ORGANISM: human
<220> FEATURE:
<221> NAME/KEY: misc_feature
<222> LOCATION: (1)..(115)
<223> OTHER INFORMATION: 12B5 antibody variable heavy chain from
      WO 01/92340

<400> SEQUENCE: 15

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Asn Tyr Ala Asp Ser Val Lys
    50                  55                  60

Gly Arg Phe Thr Ile Ser Arg Asp Asn Ala Lys Asn Ser Leu Tyr Leu
65              70                  75                  80

Gln Met Asn Ser Leu Arg Ala Glu Asp Met Ala Val Tyr Tyr Cys Ala
                85                  90                  95

Arg Gly Arg Tyr Tyr Phe Asp Tyr Trp Gly Gln Gly Thr Leu Val Thr
            100                 105                 110

Val Ser Ser
        115
```